US009096895B2

(12) United States Patent
Busk

(10) Patent No.: US 9,096,895 B2
(45) Date of Patent: Aug. 4, 2015

(54) METHOD FOR QUANTIFICATION OF SMALL RNA SPECIES

(75) Inventor: Peter Kamp Busk, Soeborg (DK)

(73) Assignee: EXIQON A/S, Vedbaek (DK)

( * ) Notice: Subject to any disclaimer, the term of this patent is extended or adjusted under 35 U.S.C. 154(b) by 871 days.

(21) Appl. No.: 13/147,562

(22) PCT Filed: Feb. 2, 2010

(86) PCT No.: PCT/DK2010/050029
§ 371 (c)(1),
(2), (4) Date: Nov. 16, 2011

(87) PCT Pub. No.: WO2010/085966
PCT Pub. Date: Aug. 5, 2010

(65) Prior Publication Data
US 2012/0071332 A1 Mar. 22, 2012

(30) Foreign Application Priority Data

Feb. 2, 2009 (DK) .................................. 2009 00156
Sep. 17, 2009 (DK) .................................. 2009 01038

(51) Int. Cl.
C12Q 1/68 (2006.01)
C07H 21/00 (2006.01)
(52) U.S. Cl.
CPC ............ *C12Q 1/6851* (2013.01); *C12Q 1/6858* (2013.01)
(58) Field of Classification Search
None
See application file for complete search history.

(56) References Cited

U.S. PATENT DOCUMENTS

| 3,687,808 | A | | 8/1972 | Merigan, Jr. et al. |
| 5,432,272 | A | | 7/1995 | Benner |
| 5,599,672 | A | * | 2/1997 | Liang et al. ................... 435/6.12 |
| 2004/0071599 | A1 | * | 4/2004 | Rusch et al. ..................... 422/99 |
| 2005/0076675 | A1 | * | 4/2005 | Bogdahn et al. ............. 65/29.12 |
| 2007/0292878 | A1 | * | 12/2007 | Raymond ........................ 435/6 |

FOREIGN PATENT DOCUMENTS

| DE | 102006038113 A1 | 2/2008 |
| EP | 1072679 A2 | 1/2001 |
| WO | 97/12896 A1 | 4/1997 |
| WO | 98/39352 A1 | 9/1998 |
| WO | 99/14226 A2 | 3/1999 |
| WO | 03/020739 A2 | 3/2003 |
| WO | 2005/098029 A2 | 10/2005 |
| WO | 2006/081284 A2 | 8/2006 |
| WO | 2007/025281 A2 | 3/2007 |
| WO | 2008/040355 A2 | 4/2008 |

OTHER PUBLICATIONS

Liang P. et al: "Differential display of eukaryotic messenger RNA by means of the polymerase chain reaction.", Science (New York, N.Y.) Aug 14, 1992, vol. 257, No. 5072, Aug. 14, 1992, pp. 967-971, ISSN: 0036-8075.
Chen et al: "Real-time quantification of Micro-RNAs by stem-loop RT-PCR", Nucleic Acids Research, Information Retrieval Ltd, vol. 33, No. 20, Jan. 1, 2005, p. E179, XP008132134, ISSN: 0305-1048,001: 10.1093/NAR/GNI178.
Chen et al: "Real-time quantification of microRNAs by stem-loop RT-PCR, Supplementary data", 2005, EPO Form 2906 01.91 TRI Retrieved from the Internet: URL:http://nar.oxfordjournals.org/contentisuppl/ 200511 /18/33.20.e179.DC1 /gni178_S2.pdf [retrieved on Sep. 10, 2013].
Communication pursuant to Article 94(3) EPC received from the European Patent Office, for a corresponding European patent application No. 10 706 492.5-140, Sep. 2013.
Barbarotto et al.; MicroRNAs and cancer: profile, profile, profile; Int. J. Cancer 122(5):969-977, 2008.
Cook; Medicinal chemistry of antisense oligonucleotides—future opportunities; Anti-Cancer Drug Design 6(6):585-607; 1991.
Englisch et al.; Chemically Modified Oligonucleotides as Probes and Inhibitors; Angewandte Chemie, International Edition 30(6):613-629; 1991.
Freier and Altmann; The ups and downs of nucleic acid duplex stability: Structure-stability studies on chemically-modified DNA:RNA duplexes; Nucleic Acid Research 25(22):4429-4443; 1997.
Gilad et al.; Serum microRNAs are promising novel biomarkers; PLoS One 3(9):e3148; Sep. 5, 2008.
Kibbe; OligoCalc: an online oligonucleotide properties calculator; Nucleic Acids Res vol. 35:W43-W46; 2007.
Kroschwitz Ed., Concise Encyclopedia of Polymer Science and Engineering; John Wiley & Sons, pp. 858-859, 1990.
Lagos-Quintana et al.; Reports: Identification of Novel Genes Coding for Small Expressed RNAs; Science 294:853-858; 2001.
Lau et al.; An Abundant Class of Tiny RNAs with Probable Regulatory Roles in *Caenorhabditis elegans*; Science 294:858-862; 2001.
Lee and Ambros; An Extensive Class of Small RNAs in *Caenorhabditis elegans*; Science 294:862-864; 2001.
Lee et al.; The *C. elegans* heterochronic gene lin-4 encodes small RNAs with antisense complementarity to lin-14; Cell 75(5):843-854; 1993.
Liang et al.; Characterization of microRNA expression profiles in normal human tissues; BMC Genomics 8:166; 2007.
Lim et al.; Mustering the micromanagers, Nature Biotechnol. 25(9):996-7; 2007.

(Continued)

*Primary Examiner* — Jennifer Dunston
*Assistant Examiner* — Addison D Ault
(74) *Attorney, Agent, or Firm* — McDonnell Boehnen Hulbert & Berghoff LLP

(57) ABSTRACT

The present invention relates to a method for amplification and quantification of microRNA molecules using quantitative reverse transcription polymerase chain reaction (qRT-PCR) technology. The method comprise the steps of (a) producing cDNA molecules complementary' to microRNAs in a sample using polyadenylation and primer extension by reverse transcription, and (b) amplification and quantification of the cDNAs by qPCR using microRNA specific primer sets of forward and reverse primers containing LNA monomers.

36 Claims, 10 Drawing Sheets

(56) References Cited

OTHER PUBLICATIONS

LNA Probe Tm Predictor (http://www.exiqon.com/oligo-tools) (last visited Jul. 18, 2012).

Mesmaeker et. al.; Backbone modifications in oligonucleotides and peptide nucleic acid systems; Current Opinion in Structural Biology 5(3):343-355; 1995.

miRBase database version 12.0 (http://microma.sanger.ac.uk or mirbase.org) (last visited Jul. 18, 2012).

miR2Disease Base (http://www.mir2disease.org/) (last visited Jul. 18, 2012).

Raymond et al.; Simple, quantitative primer-extension PCR assay for direct monitoring of microRNAs and short-interfering RNAs; RNA 11(11):1737-44; Nov. 2005.

Sanghvi; Heterocyclic Base Modifications in Nucleic Acids and Their Applications in Antisense Oligonucleotides; Antisense Research and Application, Ed. S. T. Crooke and B. Lebleu, CRC Press, in chapter 15; pp. 273-288; 1993.

Sharbati-Tehrani et al.; miR-Q: a novel quantitative RT-PCR approach for the expression profiling of small RNA molecules such as miRNAs in a complex sample; BMC Molecular Biology 9:34; 2008.

Wightman et al.; Posttranscriptional regulation of the heterochronic gene lin-14 by lin-4 mediates temporal pattern formation in *C. elegans*; Cell 75(5):855-862; 1993.

Ylikoski et al.; Quantitative reverse transcription-PCR assay with an internal standard for the detection of prostate-specific antigen mRNA; Clinical Chemistry, American Association for Clinical Chemistry, Washington, DC vol. 45 (9):1397-1407; Sep. 1, 1999; XP002579932.

Zhang et al; The cell growth suppressor, mir-126, targets IRS-1; Biochemical and biophysical Research Communications, Academic Press Inc, Orlando, FL, US LNKD-DOI:10.1016/J. BBRC.2008.09. 089, vol. 377 (1):136-140; Dec. 5, 2008; XP025587437.

Jensen et al., Research Article: Evaluation of two commercial global miRNA expression profiling platforms for detection of less abundant miRNAs, BMC Genomics, 12:435, 2011.

Mestdagh et al., Evaluation of quantitative miRN a expression platforms in the microRN a quality control (miRQC) study, Nat Methods, 11(9):971, Sep. 2014.

\* cited by examiner

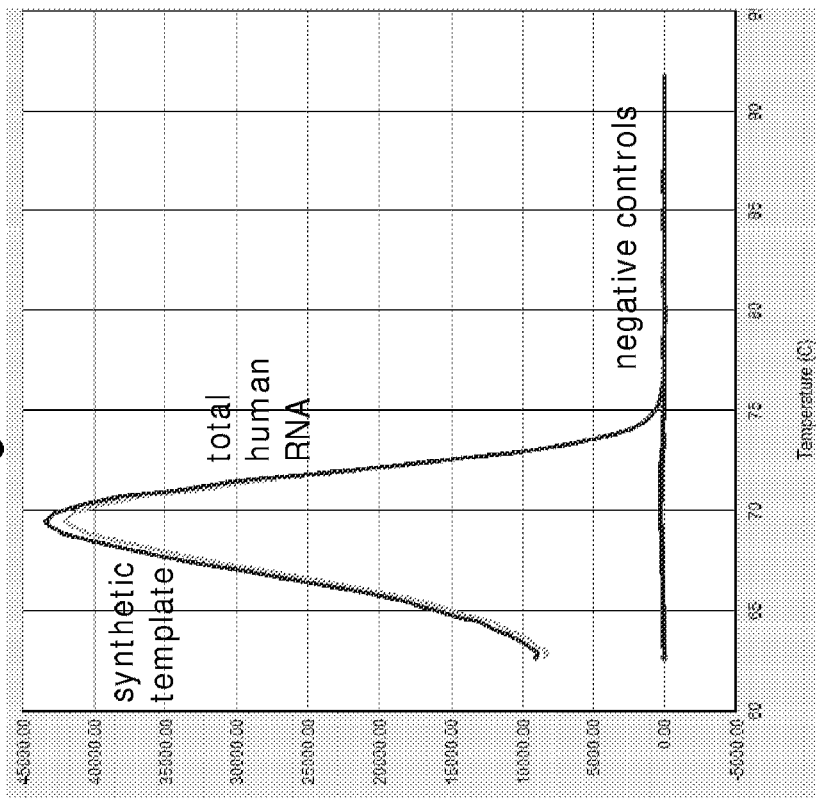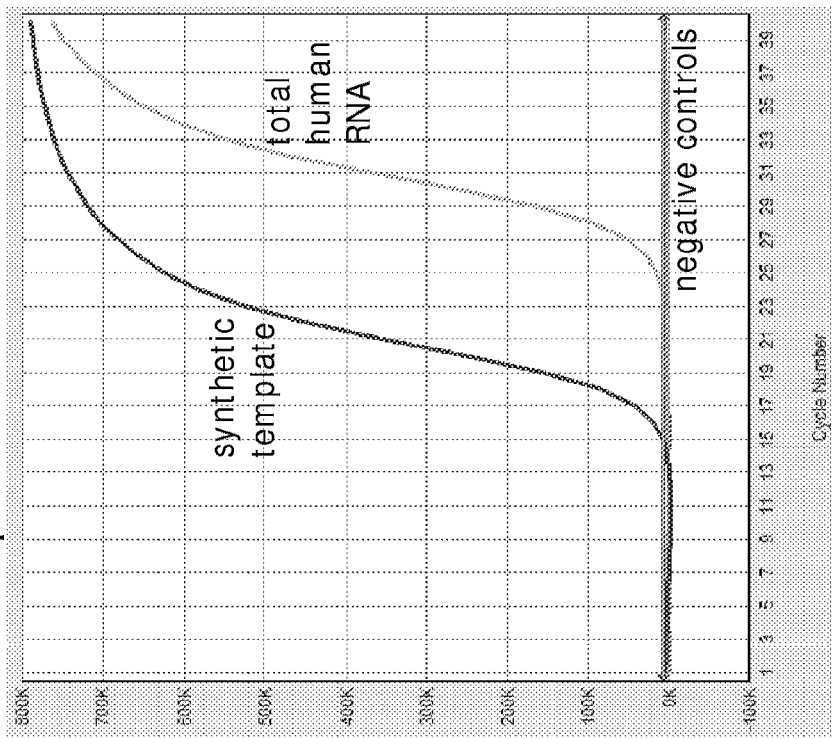
Fig. 2

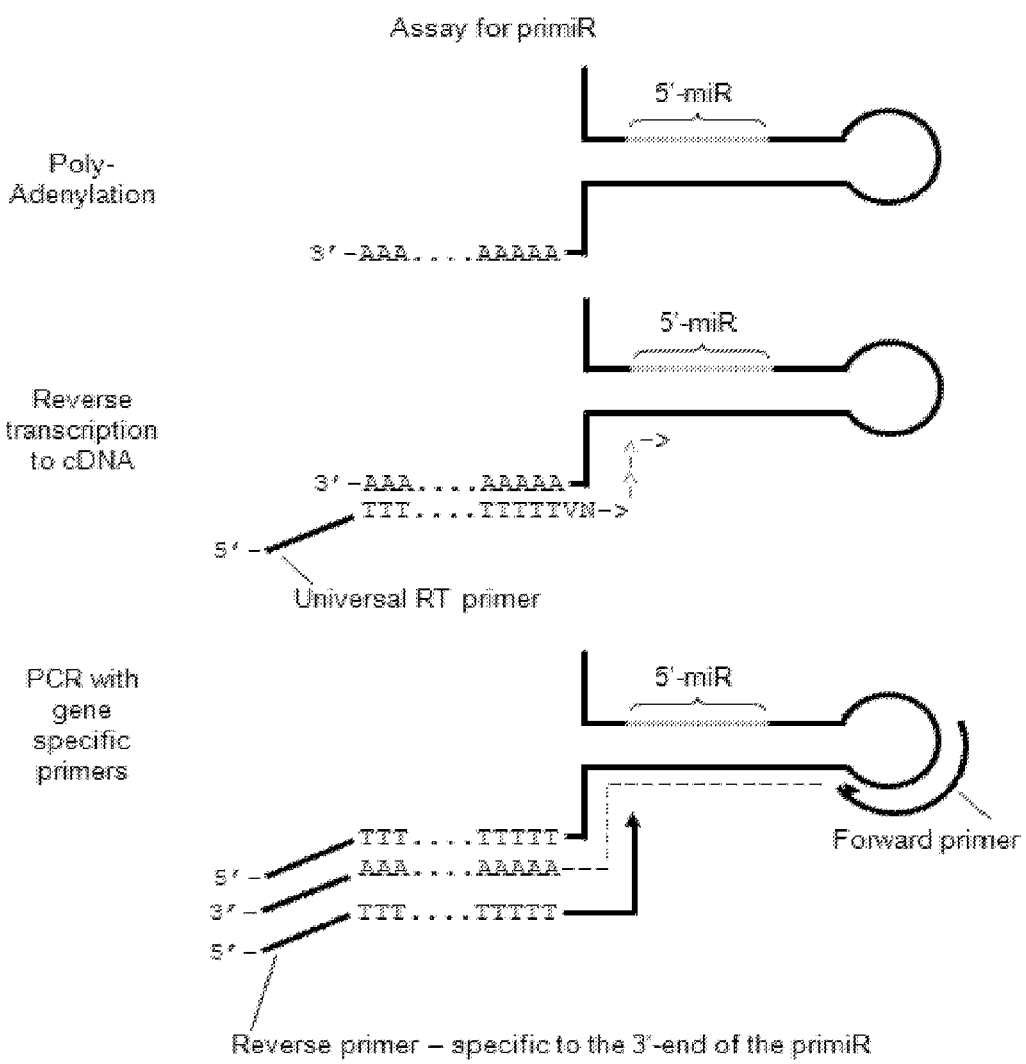

SEQUENCE LISTING

<160> NUMBER OF SEQ ID NOS: 132

<210> SEQ ID NO 1
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: C is mC

<400> SEQUENCE: 1
ttcaccacct tctcca                                                 16

<210> SEQ ID NO 2
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: Locked nucleic acid

<400> SEQUENCE: 2
cttttttttt tttttgctg ggt                                          23

<210> SEQ ID NO 3
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Locked nucleic acid

<400> SEQUENCE: 3
tgacacggag gtactag                                                17

<210> SEQ ID NO 4
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Locked nucleic acid

<400> SEQUENCE: 4
tgacacggag gtactagttt ttttttttt tt                                32

```
<210> SEQ ID NO 5
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Locked nucleic acid
<220> FEATURE:
<221> NAME/KEY: misc_feature
<222> LOCATION: (24)..(24)
<223> OTHER INFORMATION: v =  any of a, g or c
<220> FEATURE:
<221> NAME/KEY: misc_feature
<222> LOCATION: (25)..(25)
<223> OTHER INFORMATION: n =  any of a, g, c or t

<400> SEQUENCE: 5
ggtactagtt tttttttttt tttvn                                    25

<210> SEQ ID NO 6
<211> LENGTH: 59
<212> TYPE: DNA
<213> ORGANISM: Artificial Sequence
<220> FEATURE:
<223> OTHER INFORMATION: Synthetic

<400> SEQUENCE: 6
tgcggtgaca cggaggtact agttttttttt ttttttaac tatacaacct actacctca    59

<210> SEQ ID NO 7
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (4)..(4)
<223> OTHER INFORMATION: Locked nucleic acid

<400> SEQUENCE: 7
tgaggtagta ggttg                                               15

<210> SEQ ID NO 8
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Locked nucleic acid

<400> SEQUENCE: 8
cggtgacacg gaggtactag tttttttttt tttttaacta ta                 42

<210> SEQ ID NO 9
<211> LENGTH: 42
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (38)..(38)
<223> OTHER INFORMATION: c is mC

<400> SEQUENCE: 9
cggtgacacg gaggtactag ttttttttt ttttaacta ta                    42

<210> SEQ ID NO 10
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (4)..(4)
<223> OTHER INFORMATION: c is mC

<400> SEQUENCE: 10
tagcagcacg taaa                                                 14

<210> SEQ ID NO 11
<211> LENGTH: 36
<212> TYPE: DNA
<213> ORGANISM: Artificial Sequence
<220> FEATURE:
<223> OTHER INFORMATION: Synthetic

<400> SEQUENCE: 11
cacggaggta ctagttttt ttttttttc gccaat                           36

<210> SEQ ID NO 12
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (30)..(30)
<223> OTHER INFORMATION: c is mC

<400> SEQUENCE: 12
cacggaggta ctagttttt ttttttttc gccaat                           36

<210> SEQ ID NO 13
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (4)..(4)
<223> OTHER INFORMATION: c is mC

<400> SEQUENCE: 13
tagcttatca gactgatg                                             18

<210> SEQ ID NO 14
<211> LENGTH: 41
```

<212> TYPE: DNA
<213> ORGANISM: Artificial Sequence
<220> FEATURE:
<223> OTHER INFORMATION: Synthetic

<400> SEQUENCE: 14
gcggtgacac ggaggtacta gttttttttt ttttttcaa c                         41

<210> SEQ ID NO 15
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (38)..(38)
<223> OTHER INFORMATION: c is mC

<400> SEQUENCE: 15
gcggtgacac ggaggtacta gttttttttt ttttttcaa c                         41

<210> SEQ ID NO 16
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: c is mC
<220> FEATURE:
<221> NAME/KEY: misc_feature
<222> LOCATION: (5)..(5)
<223> OTHER INFORMATION: c is mC

<400> SEQUENCE: 16
atcacattgc cag                                                        13

<210> SEQ ID NO 17
<211> LENGTH: 39
<212> TYPE: DNA
<213> ORGANISM: Artificial Sequence
<220> FEATURE:
<223> OTHER INFORMATION: Synthetic

<400> SEQUENCE: 17
tgacacggag gtactagttt tttttttttt ttggaaatc                            39

<210> SEQ ID NO 18
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid

<400> SEQUENCE: 18
tgacacggag gtactagttt tttttttttt ttggaaatc                            39

<210> SEQ ID NO 19
<211> LENGTH: 14
<212> TYPE: DNA
<213> ORGANISM: Artificial Sequence
<220> FEATURE:

```
<223> OTHER INFORMATION: Synthetic
<220> FEATURE:
<221> NAME/KEY: misc_feature
<222> LOCATION: (2)..(2)
<223> OTHER INFORMATION: c is mC
<220> FEATURE:
<221> NAME/KEY: misc_feature
<222> LOCATION: (4)..(4)
<223> OTHER INFORMATION: c is mC

<400> SEQUENCE: 19
tctcccaacc cttg                                                          14

<210> SEQ ID NO 20
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: c is mC

<400> SEQUENCE: 20
tgacacggag gtactagttt tttttttttt ttcactggta                               40

<210> SEQ ID NO 21
<211> LENGTH: 40
<212> TYPE: DNA
<213> ORGANISM: Artificial Sequence
<220> FEATURE:
<223> OTHER INFORMATION: Synthetic

<400> SEQUENCE: 21
tgacacggag gtactagttt tttttttttt ttcactggta                               40

<210> SEQ ID NO 22
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (7)..(7)
<223> OTHER INFORMATION: c is mC

<400> SEQUENCE: 22
ataagacgag caaaaag                                                       17

<210> SEQ ID NO 23
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: c is mC

<400> SEQUENCE: 23
cggtgacacg gaggtactag tttttttttt ttttacaag c                              41
```

```
<210> SEQ ID NO 24
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (36)..(36)
<223> OTHER INFORMATION: Locked nucleic acid

<400> SEQUENCE: 24
cggtgacacg gaggtactag ttttttttt ttttacaag c                           41

<210> SEQ ID NO 25
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (35)..(35)
<223> OTHER INFORMATION: Locked nucleic acid

<400> SEQUENCE: 25
cggtgacacg gaggtactag ttttttttt ttttacaag c                           41

<210> SEQ ID NO 26
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid

<400> SEQUENCE: 26
taaggcacgc ggtga                                                      15

<210> SEQ ID NO 27
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: c is mC
<220> FEATURE:
<221> NAME/KEY: misc_feature
<222> LOCATION: (8)..(8)
<223> OTHER INFORMATION: Locked nucleic acid

<400> SEQUENCE: 27
ctgtctttgg ttatctag                                                   18

<210> SEQ ID NO 28
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: c is mC
<220> FEATURE:
```

```
<221> NAME/KEY: misc_feature
<222> LOCATION: (7)..(7)
<223> OTHER INFORMATION: c is mC

<400> SEQUENCE: 28
aacattcaac gctgt                                                    15

<210> SEQ ID NO 29
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: c is mC
<220> FEATURE:
<221> NAME/KEY: misc_feature
<222> LOCATION: (4)..(4)
<223> OTHER INFORMATION: c is mC

<400> SEQUENCE: 29
tcacagtgaa ccggt                                                    15

<210> SEQ ID NO 30
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 30
ttgaaaggct atttc                                                    15

<210> SEQ ID NO 31
<211> LENGTH: 15
<212> TYPE: DNA
<213> ORGANISM: Artificial Sequence
<220> FEATURE:
<223> OTHER INFORMATION: Synthetic

<400> SEQUENCE: 31
ctggccctct ctgcc                                                    15

<210> SEQ ID NO 32
<211> LENGTH: 17
<212> TYPE: DNA
<213> ORGANISM: Artificial Sequence
<220> FEATURE:
<223> OTHER INFORMATION: Synthetic

<400> SEQUENCE: 32
cgcatcccct agggcat                                                  17

<210> SEQ ID NO 33
<211> LENGTH: 15
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (4)..(4)
<223> OTHER INFORMATION: Locked nucleic acid

<400> SEQUENCE: 33
ctaggtatgg tccca                                                    15

<210> SEQ ID NO 34
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 34
tggcagtgtc ttagc                                                    15

<210> SEQ ID NO 35
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 35
cagtgcaatg ttaaaag                                                  17

<210> SEQ ID NO 36
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (4)..(4)
<223> OTHER INFORMATION: Locked nucleic acid

<400> SEQUENCE: 36
tggaatgtaa agaagt                                                   16

<210> SEQ ID NO 37
<211> LENGTH: 13
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (3)..(3)
<223> OTHER INFORMATION: c is mC
<220> FEATURE:
<221> NAME/KEY: misc_feature
<222> LOCATION: (5)..(5)
<223> OTHER INFORMATION: c is mC

<400> SEQUENCE: 37
atcacattgc cag                                                          13

<210> SEQ ID NO 38
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (4)..(4)
<223> OTHER INFORMATION: Locked nucleic acid

<400> SEQUENCE: 38
tttggtcccc ttcaa                                                        15

<210> SEQ ID NO 39
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (4)..(4)
<223> OTHER INFORMATION: Locked nucleic acid

<400> SEQUENCE: 39
tttggtcccc ttcaa                                                        15

<210> SEQ ID NO 40
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 40
caaagtgctg ttcgtg                                                       16

<210> SEQ ID NO 41
<211> LENGTH: 16
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (3)..(3)
<223> OTHER INFORMATION: c is mC
<220> FEATURE:
<221> NAME/KEY: misc_feature
<222> LOCATION: (7)..(7)
<223> OTHER INFORMATION: c is mC

<400> SEQUENCE: 41
aacattcatt gctgtc                                                         16

<210> SEQ ID NO 42
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (6)..(6)
<223> OTHER INFORMATION: c is mC

<400> SEQUENCE: 42
tggctcagtt cagca                                                          15

<210> SEQ ID NO 43
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (32)..(32)
<223> OTHER INFORMATION: Locked nucleic acid

<400> SEQUENCE: 43
tgacacggag gtactagttt tttttttttt ttggcat                                  37

<210> SEQ ID NO 44
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: c is mC

<400> SEQUENCE: 44
tgacacggag gtactagttt tttttttttt ttcatacag                                39

<210> SEQ ID NO 45
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(34)
<223> OTHER INFORMATION: c is mC
```

```
<400> SEQUENCE: 45
tgacacggag gtactagttt ttttttttt ttactcac                          38

<210> SEQ ID NO 46
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid

<400> SEQUENCE: 46
tgacacggag gtactagttt ttttttttt ttaaagaga                         39

<210> SEQ ID NO 47
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid

<400> SEQUENCE: 47
tgacacggag gtactagttt ttttttttt ttgacca                           37

<210> SEQ ID NO 48
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid

<400> SEQUENCE: 48
tgacacggag gtactagttt ttttttttt ttacggaa                          38

<210> SEQ ID NO 49
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid

<400> SEQUENCE: 49
tgacacggag gtactagttt ttttttttt ttacacca                          38

<210> SEQ ID NO 50
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid
```

```
<400> SEQUENCE: 50
tgacacggag gtactagttt tttttttttt ttggatc                              37

<210> SEQ ID NO 51
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(34)
<223> OTHER INFORMATION: c is mC

<400> SEQUENCE: 51
tgacacggag gtactagttt tttttttttt ttacaacca                            39

<210> SEQ ID NO 52
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid

<400> SEQUENCE: 52
tgacacggag gtactagttt tttttttttt ttatgc                               36

<210> SEQ ID NO 53
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid

<400> SEQUENCE: 53
tgacacggag gtactagttt tttttttttt ttatacata                            39

<210> SEQ ID NO 54
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (35)..(35)
<223> OTHER INFORMATION: Locked nucleic acid

<400> SEQUENCE: 54
tgacacggag gtactagttt tttttttttt ttggtaatc                            39

<210> SEQ ID NO 55
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
```

<223> OTHER INFORMATION: Locked nucleic acid

<400> SEQUENCE: 55
tgacacggag gtactagttt tttttttttt ttgagctg                    38

<210> SEQ ID NO 56
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid

<400> SEQUENCE: 56
tgacacggag gtactagttt tttttttttt ttagctg                    37

<210> SEQ ID NO 57
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: c is mC

<400> SEQUENCE: 57
tgacacggag gtactagttt tttttttttt ttctacctg                  39

<210> SEQ ID NO 58
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid

<400> SEQUENCE: 58
tgacacggag gtactagttt tttttttttt ttaccca                    37

<210> SEQ ID NO 59
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (32)..(32)
<223> OTHER INFORMATION: c is mC

<400> SEQUENCE: 59
tgacacggag gtactagttt tttttttttt tctgttc                    37

<210> SEQ ID NO 60
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature

```
<222> LOCATION: (5)..(5)
<223> OTHER INFORMATION: Locked nucleic acid

<400> SEQUENCE: 60
ctgtgagaac tgaattcca                                              19

<210> SEQ ID NO 61
<211> LENGTH: 15
<212> TYPE: DNA
<213> ORGANISM: Artificial Sequence
<220> FEATURE:
<223> OTHER INFORMATION: Synthetic

<400> SEQUENCE: 61
tgccctgtgg actca                                                  15

<210> SEQ ID NO 62
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: c is mC
<220> FEATURE:
<221> NAME/KEY: misc_feature
<222> LOCATION: (11)..(11)
<223> OTHER INFORMATION: Locked nucleic acid

<400> SEQUENCE: 62
ctgtaatact gtctggta                                               18

<210> SEQ ID NO 63
<211> LENGTH: 18
<212> TYPE: DNA
<213> ORGANISM: Artificial Sequence
<220> FEATURE:
<223> OTHER INFORMATION: Synthetic

<400> SEQUENCE: 63
aactggccta caaagtcc                                               18

<210> SEQ ID NO 64
<211> LENGTH: 14
<212> TYPE: DNA
<213> ORGANISM: Artificial Sequence
<220> FEATURE:
<223> OTHER INFORMATION: Synthetic

<400> SEQUENCE: 64
gtctttgcgg gcga                                                   14

<210> SEQ ID NO 65
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: c is mC

<400> SEQUENCE: 65
aactggccct caaag                                                  15
```

```
<210> SEQ ID NO 66
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: c is mC
<220> FEATURE:
<221> NAME/KEY: misc_feature
<222> LOCATION: (7)..(7)
<223> OTHER INFORMATION: Locked nucleic acid

<400> SEQUENCE: 66
tctggctccg tgtcttca                                                 18

<210> SEQ ID NO 67
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: c is mC
<220> FEATURE:
<221> NAME/KEY: misc_feature
<222> LOCATION: (5)..(5)
<223> OTHER INFORMATION: Locked nucleic acid

<400> SEQUENCE: 67
aactgtttgc agaggaa                                                  17

<210> SEQ ID NO 68
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: c is mC
<220> FEATURE:
<221> NAME/KEY: misc_feature
<222> LOCATION: (6)..(6)
<223> OTHER INFORMATION: c is mC

<400> SEQUENCE: 68
ctcatctgca aagaagta                                                 18

<210> SEQ ID NO 69
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (7)..(7)
<223> OTHER INFORMATION: c is mC

<400> SEQUENCE: 69
tgtaaacatc ctacactc                                                 18
```

-continued

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
ctgcaatcac taactccact                                               20

<210> SEQ ID NO 71
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Locked nucleic acid

<400> SEQUENCE: 71
aggcagtgta gttagctg                                                 18

<210> SEQ ID NO 72
<211> LENGTH: 18
<212> TYPE: DNA
<213> ORGANISM: Artificial Sequence
<220> FEATURE:
<223> OTHER INFORMATION: Synthetic

<400> SEQUENCE: 72
tgtgactggt tgaccaga                                                 18

<210> SEQ ID NO 73
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Locked nucleic acid

<400> SEQUENCE: 73
ctgaggaagc cctgga                                                   16

<210> SEQ ID NO 74
<211> LENGTH: 18
<212> TYPE: DNA
<213> ORGANISM: Artificial Sequence
<220> FEATURE:
<223> OTHER INFORMATION: Synthetic

<400> SEQUENCE: 74
ctgggatctc cggggtct                                                 18

<210> SEQ ID NO 75
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)

<223> OTHER INFORMATION: Locked nucleic acid

<400> SEQUENCE: 75
cgtactagtt tttttttttt tttagcct        28

<210> SEQ ID NO 76
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: c is mC

<400> SEQUENCE: 76
gtactagttt tttttttttt ttccagaac       29

<210> SEQ ID NO 77
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: Locked nucleic acid

<400> SEQUENCE: 77
gtactagttt tttttttttt ttacggtt        28

<210> SEQ ID NO 78
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: c is mC

<400> SEQUENCE: 78
gtactagttt tttttttttt ttactgg         27

<210> SEQ ID NO 79
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: c is mC

<400> SEQUENCE: 79
ggtactagtt tttttttttt tttcatct        28

<210> SEQ ID NO 80
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (27)..(27)
<223> OTHER INFORMATION: c is mC

<400> SEQUENCE: 80
gaggtactag tttttttttt tttttttcatc t            31

<210> SEQ ID NO 81
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: Locked nucleic acid

<400> SEQUENCE: 81
tagttttttt ttttttttgg gagtg            25

<210> SEQ ID NO 82
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: c is mC

<400> SEQUENCE: 82
gtactagttt tttttttttt ttcagtt            27

<210> SEQ ID NO 83
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: c is mC

<400> SEQUENCE: 83
gtactagttt tttttttttt ttcactt            27

<210> SEQ ID NO 84
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: Locked nucleic acid

<400> SEQUENCE: 84
gtactagttt tttttttttt ttagctga            28

<210> SEQ ID NO 85
<211> LENGTH: 29
<212> TYPE: DNA
<213> ORGANISM: Artificial Sequence
<220> FEATURE:
<223> OTHER INFORMATION: Synthetic
<220> FEATURE:

```
<221> NAME/KEY: misc_feature
<222> LOCATION: (26)..(26)
<223> OTHER INFORMATION: Locked nucleic acid

<400> SEQUENCE: 85
gaggtactag ttttttttt tttttatgg                                          29

<210> SEQ ID NO 86
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Locked nucleic acid

<400> SEQUENCE: 86
tactagtttt ttttttttt tgcaatca                                           28

<210> SEQ ID NO 87
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Locked nucleic acid

<400> SEQUENCE: 87
gtactagttt ttttttttt ttcccct                                            27

<210> SEQ ID NO 88
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: c is mC

<400> SEQUENCE: 88
gtactagttt ttttttttt ttctcca                                            27

<210> SEQ ID NO 89
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (25)..(25)
<223> OTHER INFORMATION: Locked nucleic acid

<400> SEQUENCE: 89
aggtactagt ttttttttt tttttaacca                                         29

<210> SEQ ID NO 90
<211> LENGTH: 22
<212> TYPE: RNA
<213> ORGANISM: Homo sapiens

<400> SEQUENCE: 90
```

-continued ugagguagua gguuguauag uu                                                22

<210> SEQ ID NO 91
<211> LENGTH: 22
<212> TYPE: RNA
<213> ORGANISM: Homo sapiens

<400> SEQUENCE: 91
ugagguagua gauuguauag uu                                                22

<210> SEQ ID NO 92
<211> LENGTH: 22
<212> TYPE: RNA
<213> ORGANISM: Homo sapiens

<400> SEQUENCE: 92
ugagguagua gguuguaugg uu                                                22

<210> SEQ ID NO 93
<211> LENGTH: 22
<212> TYPE: RNA
<213> ORGANISM: Homo sapiens

<400> SEQUENCE: 93
ugagguagga gguuguauag uu                                                22

<210> SEQ ID NO 94
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (28)..(28)
<223> OTHER INFORMATION: Locked nucleic acid

<400> SEQUENCE: 94
cggaggtact agttttttttt tttttttaac tat                                    33

<210> SEQ ID NO 95
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: c is mC
<220> FEATURE:
<221> NAME/KEY: misc_feature
<222> LOCATION: (5)..(5)
<223> OTHER INFORMATION: c is mC

<400> SEQUENCE: 95
ttcacagtgg ctaag                                                        15

<210> SEQ ID NO 96
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)

<223> OTHER INFORMATION: Locked nucleic acid

<400> SEQUENCE: 96
tgacacggag gtactagttt ttttttttt ttgcaga                                37

<210> SEQ ID NO 97
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (9)..(9)
<223> OTHER INFORMATION: Locked nucleic acid

<400> SEQUENCE: 97
ctgtagcagc acagaa                                                     16

<210> SEQ ID NO 98
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid

<400> SEQUENCE: 98
tgacacggag gtactagttt ttttttttt ttgccaat                               38

<210> SEQ ID NO 99
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 99
taccctgtag atccgaa                                                    17

<210> SEQ ID NO 100
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: c is mC

<400> SEQUENCE: 100
tgacacggag gtactagttt ttttttttt ttcacaaat                              39

```
<210> SEQ ID NO 101
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid

<400> SEQUENCE: 101
tgtgtaagga attttgtggt                                               20

<210> SEQ ID NO 102
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (36)..(36)
<223> OTHER INFORMATION: Locked nucleic acid

<400> SEQUENCE: 102
gaggtactag ttttttttt tttttattc                                      29

<210> SEQ ID NO 103
<211> LENGTH: 22
<212> TYPE: RNA
<213> ORGANISM: Homo sapiens

<400> SEQUENCE: 103
gugaaauguu uaggaccacu ag                                            22

<210> SEQ ID NO 104
<211> LENGTH: 60
<212> TYPE: RNA
<213> ORGANISM: Homo sapiens

<400> SEQUENCE: 104 aggguucuu aacaguucaa caguucugua gcgcaauugu gaaauguuua ggaccacuag    60

<210> SEQ ID NO 105
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid

<400> SEQUENCE: 105
tgacacggag gtactagttt ttttttttt ttctag                              36

<210> SEQ ID NO 106
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Locked nucleic acid
<220> FEATURE:
```

<221> NAME/KEY: misc_feature
<222> LOCATION: (8)..(8)
<223> OTHER INFORMATION: Locked nucleic acid

<400> SEQUENCE: 106
gtgaaatgtt taggacca                                               18

<210> SEQ ID NO 107
<211> LENGTH: 20
<212> TYPE: DNA
<213> ORGANISM: Artificial Sequence
<220> FEATURE:
<223> OTHER INFORMATION: Synthetic

<400> SEQUENCE: 107
cagttcaaca gttctgtagc                                             20

<210> SEQ ID NO 108
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid

<400> SEQUENCE: 108
tgacacggag gtactagttt tttttttttt ttcaaacac                        39

<210> SEQ ID NO 109
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: Locked nucleic acid

<400> SEQUENCE: 109
gtactagttt tttttttttt ttccaca                                     27

<210> SEQ ID NO 110
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: Locked nucleic acid

<400> SEQUENCE: 110
gaggtactag tttttttttt tttttattta g                                31

<210> SEQ ID NO 111
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: Locked nucleic acid

<400> SEQUENCE: 111
gtactagttt ttttttttttt ttggct                                              26

<210> SEQ ID NO 112
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: Locked nucleic acid

<400> SEQUENCE: 112
gtactagttt ttttttttttt ttcgcat                                             27

<210> SEQ ID NO 113
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid

<400> SEQUENCE: 113
tgacacggag gtactagttt ttttttttttt ttagctg                                  37

<210> SEQ ID NO 114
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid

<400> SEQUENCE: 114
tgacacggag gtactagttt ttttttttttt ttatacata                                39

<210> SEQ ID NO 115
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 115
tggagtgtga caatg                                                           15

<210> SEQ ID NO 116
<211> LENGTH: 16
<212> TYPE: DNA
<213> ORGANISM: Artificial Sequence
<220> FEATURE:

```
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid

<400> SEQUENCE: 116
tgtaacagca actcca                                                          16

<210> SEQ ID NO 117
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 117
aacgccatta tcacact                                                         17

<210> SEQ ID NO 118
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (9)..(9)
<223> OTHER INFORMATION: Locked nucleic acid

<400> SEQUENCE: 118
tgactgacct atgaattgac                                                      20

<210> SEQ ID NO 119
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Locked nucleic acid

<400> SEQUENCE: 119
ctgtcgtacc gtgagta                                                         17

<210> SEQ ID NO 120
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (2)..(2)
<223> OTHER INFORMATION: Locked nucleic acid
<220> FEATURE:
<221> NAME/KEY: misc_feature
<222> LOCATION: (4)..(4)
<223> OTHER INFORMATION: Locked nucleic acid

<400> SEQUENCE: 120
tttggtcccc ttcaa                                                       15

<210> SEQ ID NO 121
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 121
ctgtggaatg taaagaagt                                                   19

<210> SEQ ID NO 122
<211> LENGTH: 21
<212> TYPE: RNA
<213> ORGANISM: Homo sapiens

<400> SEQUENCE: 122
ugagaugaag cacuguagcu c                                                21

<210> SEQ ID NO 123
<211> LENGTH: 23
<212> TYPE: RNA
<213> ORGANISM: Homo sapiens

<400> SEQUENCE: 123
uuaaugcuaa ucgugauagg ggu                                              23

<210> SEQ ID NO 124
<211> LENGTH: 22
<212> TYPE: RNA
<213> ORGANISM: Homo sapiens

<400> SEQUENCE: 124
uggaauguaa agaaguaugu au                                               22

<210> SEQ ID NO 125
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (4)..(4)
<223> OTHER INFORMATION: Locked nucleic acid

<400> SEQUENCE: 125
```
tgagatgaag cactg                                                   15

<210> SEQ ID NO 126
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Locked nucleic acid

<400> SEQUENCE: 126
tgacacggag gtactagttt tttttttttt ttgagcta                          38

<210> SEQ ID NO 127
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Locked nucleic acid
<220> FEATURE:
<221> NAME/KEY: misc_feature
<222> LOCATION: (10)..(10)
<223> OTHER INFORMATION: Locked nucleic acid

<400> SEQUENCE: 127
gacttaatgc taatcgtgat                                              20

<210> SEQ ID NO 128
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: Locked nucleic acid

<400> SEQUENCE: 128
gtactagttt tttttttttt ttaccccta                                    29

<210> SEQ ID NO 129
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (38)..(38)
<223> OTHER INFORMATION: v =  any of a, g or c
<220> FEATURE:
<221> NAME/KEY: misc_feature
<222> LOCATION: (39)..(39)
<223> OTHER INFORMATION: n =  any of a, g, c or t

<400> SEQUENCE: 129
tgcggtgaca cggaggtact agttttttt tttttttvn                          39

<210> SEQ ID NO 130
<211> LENGTH: 10
<212> TYPE: DNA
<213> ORGANISM: Artificial Sequence

```
<220> FEATURE:
<223> OTHER INFORMATION: Synthetic polynucleotide

<400> SEQUENCE: 130
aaaaaaaaaa                                                          10

<210> SEQ ID NO 131
<211> LENGTH: 12
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(11)
<223> OTHER INFORMATION: v =  any of a, g or c
<220> FEATURE:
<221> NAME/KEY: misc_feature
<222> LOCATION: (12)..(12)
<223> OTHER INFORMATION: n =  any of c, g or a

<400> SEQUENCE: 131
tttttttttt vn                                                       12

<210> SEQ ID NO 132
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 132
tttttttttt                                                          10
```

METHOD FOR QUANTIFICATION OF SMALL RNA SPECIES

This application is the National Stage of International Application No. PCT/DK2010/050029, filed Feb. 2, 2010, which claims the benefit of foreign Denmark application PA 2009 00156, file Feb. 2, 2009, and foreign Denmark application PA 2009 01038, filed Sep. 17, 2009.

FIELD OF THE INVENTION

The present invention relates to a method for amplification and quantification of small non-coding RNA molecules using quantitative reverse transcription polymerase chain reaction (qRT-PCR) technology.

BACKGROUND OF THE INVENTION

MicroRNAs are an abundant class of approximately 22-nucleotide-noncoding RNAs, which play important regulatory roles in animal, plant and virus development. The awareness of microRNAs was initiated almost 15 years ago by the discovery of lin-4, which encode a small RNA involved in the timing and progression of the nematode in C. elegans life cycle and larval development (Lee et al. 1993 Cell 75:843-854, Wightman et al. 1993 Cell 75:855-862), but it was only recently recognized that microRNAs form a major class of ribo-regulators that have broad regulatory functions in animals (Lagos-Quintana et al. 2001 Science 294:853-858, Lau et al. 2001 Science 294:858-862, Lee and Ambros. 2001 Science 294:862-864). Since then, a revolution in the study of microRNAs have taken place, and today the miRBase database version 12.0 (http://microrna.sanger.ac.uk/) include 866 human microRNAs and the PubMed database (http://www.ncbi.nlm.nih.gov/pubmed/) encompass 3900 microRNA related articles, reflecting the interest and importance of microRNAs.

MicroRNAs are involved in the regulation of gene expression at the posttranscriptional level by degrading or blocking translation of messenger RNA targets, and it has been speculated that approximately 30% of the human genome could be regulated by microRNAs. The importance of microRNAs is also obvious due to their involvement in various cellular processes including development, growth and proliferation, apoptosis, differentiation, and various human diseases (http://www.mir2disease.org/) such as cancer and diabetes.

The importance of microRNAs in cancer is highlighted in a recent article (Barbarotto et al 2008 Int. J. Cancer. 122:969-977), which summarizes the main paradigms for the miRNA involvement in human cancers: Thus, "(i) miRNAs are altered in every type of analyzed human cancer; (ii) miRNAs act as oncogenes and tumor suppressors; (iii) miRNAs alterations may cause cancer predisposition; (iv) miRNAs profiling is a new diagnostic tool for cancer patients and (v) miRNA profiling represents prognostic tools for cancer patients.". Accordingly, methods for expression profiling and quantification of microRNAs in cells and body-fluids from cancer patients are of great importance. To address this requirement, the present invention describes the development of a new robust and reliable qRT-PCR assay for microRNA measurements.

Quantification of microRNAs by qRT-PCR procedures is very challenging due to the small size of microRNAs of only 21 to 25 nucleotides, which is the size of primers normally used for PCR. Solutions to this problem have been published in Raymond et al. RNA. 2005 November; 11(11):1737-44, Gad et al. PLoS ONE. 2008 Sep. 5; 3(9):e3148 and Sharbati-Tehrani et al. BMC Molecular Biology. 2008, 9:34. Raymond et al. describes a qRT-PCR assay that involves a gene-specific reverse transcription step followed by a SYBR® green qPCR step using a gene-specific forward primer containing locked nucleic acid (LNA) molecules and a universal reverse primer. Gilad et al. reports a qRT-PCR assay that involves a polyadenylation step, an unspecific reverse transcription step, and a qPCR step involving a gene-specific forward primer, a gene-specific TaqMan primer and a universal reverse primer. Sharbati-Tehrani et al. developed a qRT-PCR assay that involves a gene-specific reverse transcription step followed by a SYBR® green qPCR step using a gene-specific forward primer and 2 universal primers.

However, the existing techniques for quantification of microRNAs by qRT-PCR do not fulfil the present need for microRNA assays, which requires high specificity that allows discrimination between closely related microRNAs, high sensitivity, low background an a relatively simple procedure.

The present invention is characterised by only one reverse transcription reaction for all microRNAs in a sample and furthermore provides an extremely sensitive PCR method with an unmatched specificity that can be used for accurate quantification of small RNA molecules such as microRNAs.

SUMMARY OF THE INVENTION

Establishing and understanding the microRNA dysregulation patterns associated with various human diseases such as cancers, call for novel, improved technologies for detection and quantification of microRNAs in human cells and body fluids. The present invention introduces a new highly sensitive and specific assay for this purpose.

In one aspect, the present invention provides a procedure for amplifying and quantifying microRNA molecules in a sample: In the first step of the procedure complementary DNAs (cDNAs) of the microRNAs in a sample are produced by the concerted action of two enzymes in a single-tube reaction. Firstly, poly-A tails are added to the 3'-terminus of the microRNAs using a poly(A) polymerase, and secondly an extension primer is hybridized to the poly-A tail and the cDNAs are produced by a reverse transcriptase using the microRNA as template. The first step is unspecific and produces cDNAs of all microRNAs present in a sample. In the second step of the procedure specific cDNAs are amplified and quantified in a qPCR reaction using microRNA specific primer sets of forward and reverse primers containing LNA monomers.

In another aspect, the invention provides oligo nucleotide primers listed in Table 18 (SEQ ID NO 1 to SEQ ID NO 128).

The primers of the invention can be used for detecting mammalian microRNAs using the method of the invention.

In another aspect, the invention provides kits for detection of mammalian microRNAs, the kits comprising a universal extension primer and microRNA-specific forward and reverse primers sets for quantification of at least one microRNA, a subset of microRNAs or all known microRNAs.

The present invention is useful for reliable and specific quantitative microRNA assays, including assays for diagnosing and prognosing diseases such as cancer using single assays or high through-put applications on robot platforms. RNA containing samples extracted from various cell types from living organisms, such as mammals and plants and including virus infected cells may be analysed using the method of the invention.

Although the present invention mainly aims at providing a method for quantification of microRNAs the method can be used for detection and/or quantification of all types of RNA in particular all types of small noncoding RNAs.

FIGURES

FIG. 1 shows the steps involved in specific qRT-PCR of the present invention. To illustrate the principle the qRT-PCR of a microRNA serves as an example, the RNA to be analysed by the method may as well be any other small RNA molecule or even a mRNA. Step 1 is a one-tube-reaction for all microRNAs present in a sample. Step 2 is a microRNA specific qPCR using forward and reverse primer pairs for a specific microRNA. An oval indicate insertion of LNAs in forward and reverse primers. When the method is carried out in practice the miRNAs present in a sample are firstly poly-A-tailed, for example (5'-AAAAAAAAAA-3'; SEQ ID NO:130), using a poly(A) polymerase, which adds adenineresidues to the 3'-end of RNA molecules. Secondly, an extension primer, which has a poly-T-core nucleotide sequence, a 3'-end VN-degenerate motif and a 5'-end tail, for example (5'-TTTTTTTTTTVN-3'; SEQ ID NO:131 ), is annealed to the poly-A-tailed miRNA through hybridisation with the VN-poly-T-sequence of the extension primer, (N=C, G, A and T; V=C, G, and A). This primer may be referred to as the Universal RT primer. Subsequently, the extension primer is extended in a reverse transcription reaction using the miRNA as template. All of these reaction are performed in a one-tube reaction. The resulting primary extension product is composed of the extension primer and the newly synthesized DNA, which is cDNA complementary to all the miRNAs in the sample. In the next step a miRNA-specific PCR is carried out. A miRNA-specific forward primer is annealed to 3'-end of the newly synthesized cDNA and the upper-strand synthesis is carried out by extending the forward primer in a DNA-polymerization reaction using the primary extension product as template. A miRNA-specific reverse primer composed of a miRNA-specific 3'-end sequence, a poly-T-stretch, 5'-TTTTTTTTTT-3'; SEQ ID NO: 132 ), and a 5'-end tail is then hybridized to the upper-strand and the lower-strand is synthesized by extension of the reverse primer. Various demonstrations of the method of the invention are described in the EXAMPLES section.

FIG. 2 shows amplification of hsa-miR-197(Example 1) with the forward primer 5' ttmCaccaccttctcca (SEQ ID NO 1) and the reverse primer 5'-cttttttttttttttGctgggt (SEQ ID NO 2). Synthetic template: $10^7$ copies of synthetic hsa-miR-197were used for polyA tailing/RT. An amount corresponding to $10^5$copies was used for PCR. Total human RNA: 100 ng of total human RNA was used for polyA-tailing/RT (step 1). An amount corresponding to 1ng was used for PCR. Negative controls: water control and a total human RNA control without PolyA Polymerase in the RT reaction. The black line designates the result obtained with the synthetic template whereas the grey line show the result obtained with total human RNA as template. The melting curves of the result obtained with the synthetic template and the total human RNA are almost identical.

Figure 5A:
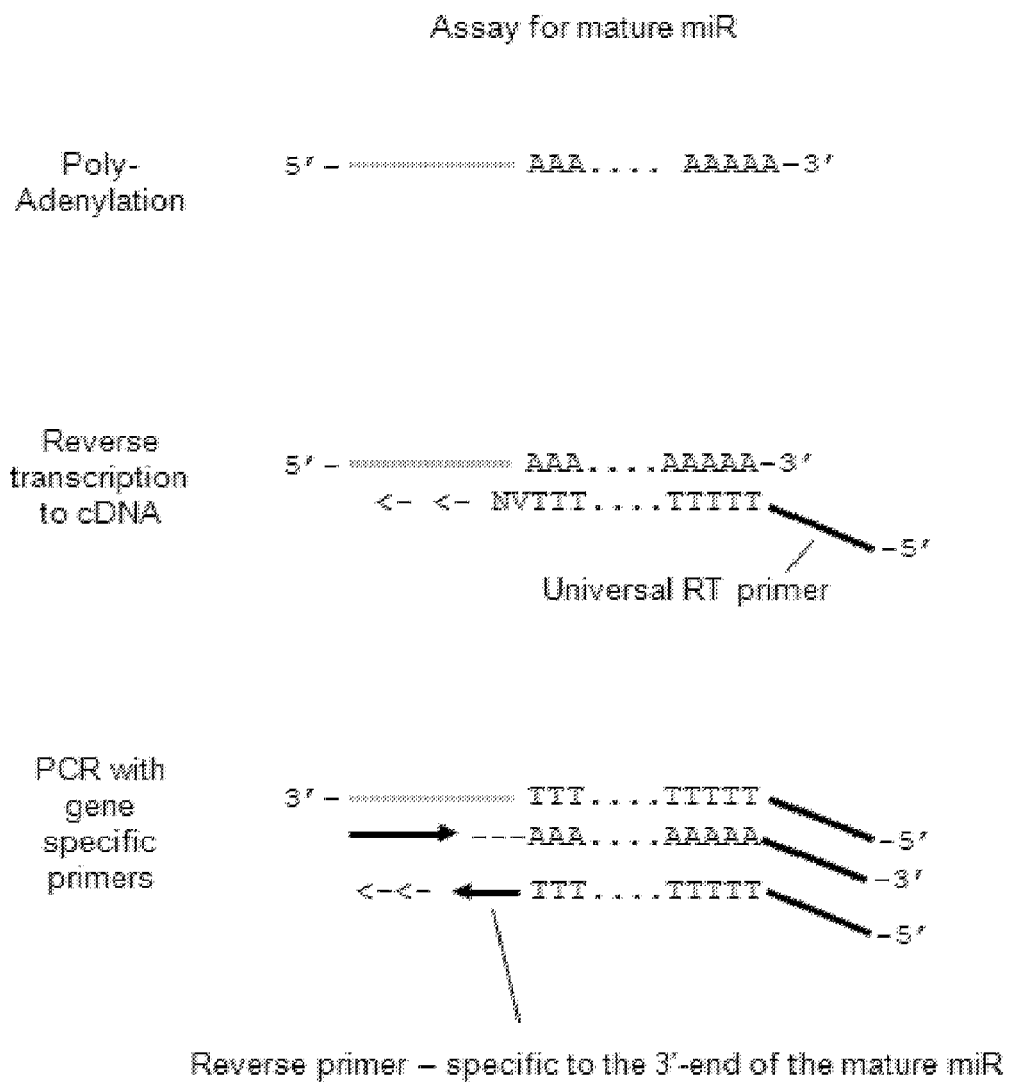
Figure 5B:
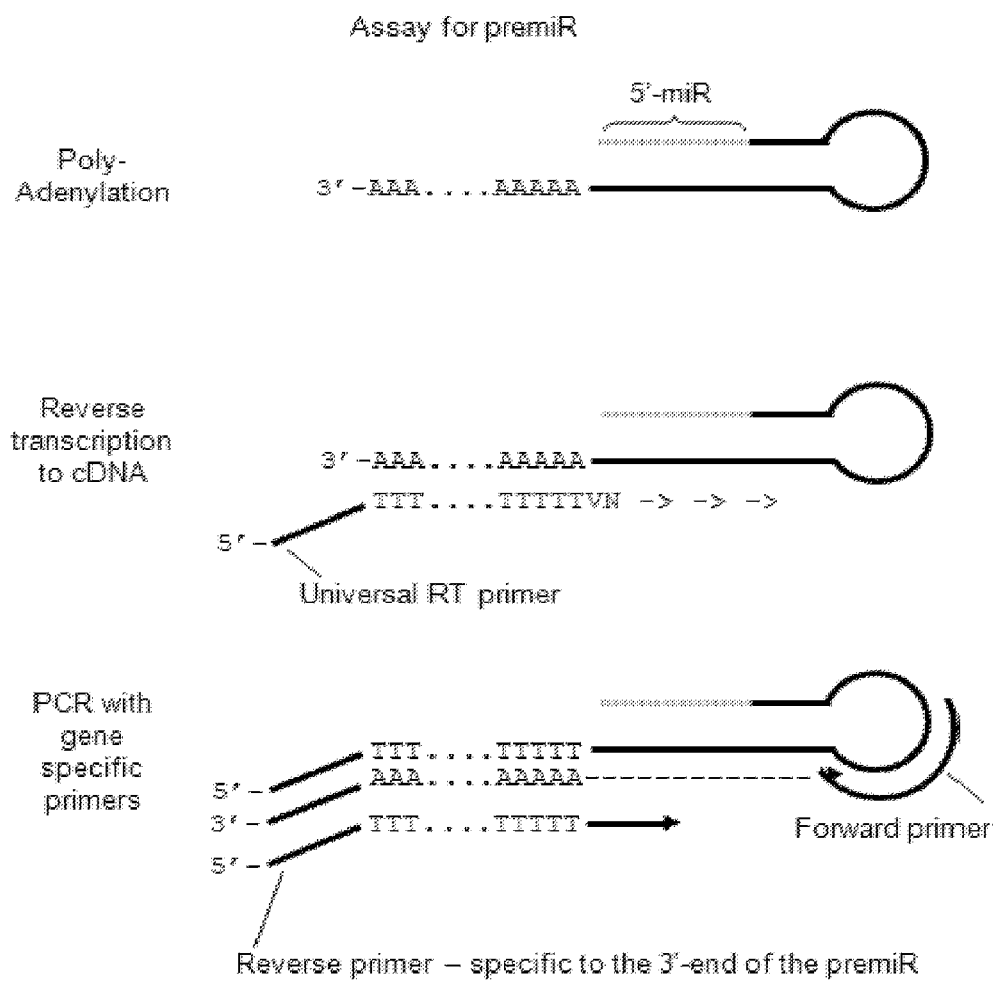

FIGS. 5A, 5B and 5C shows the method and processes that enables PCR amplification and discrimination between mature miRs, pre-miRs and pri-miRs. See example 6, 7 and 8. A) Polyadenylation of all RNA 3'-ends, for example (5'-AAAAAAAAAA-3'; SEQ ID NO:130) B) Reverse transcription of polyadenylated RNA to cDNA using the Universal RT primer (N=C, G, A and T; V=C, G, and A), for example (5'-TTTTTTTTTTVN-3'; SEQ ID NO:131 ), for example (5'-TTTTTTTTTT-3'; SEQ ID NO:132), C) MicroRNA specific PCR amplification using gene specific primers. For example, a miRNA-specific reverse primer is composed of a miRNA-specific 3'-end sequence, a poly-T-stretch, for example (5'-TTTTTTTTTT-3'; SEQ ID NO:132), and a 5'-end tail. Note that the site of polyadenylation in combination with the gene specific reverse primers ensures specific detection of each of the individual molecules mature miRs, pre-miRs and pd-miRs. FIG. 5A illustrate the assay used for assaying mature miRs. FIG. 5B illustrate the assay used for assaying pre-miRs and FIG. 5C illustrate the assay used for assaying pri-miRs.

Figure 6:
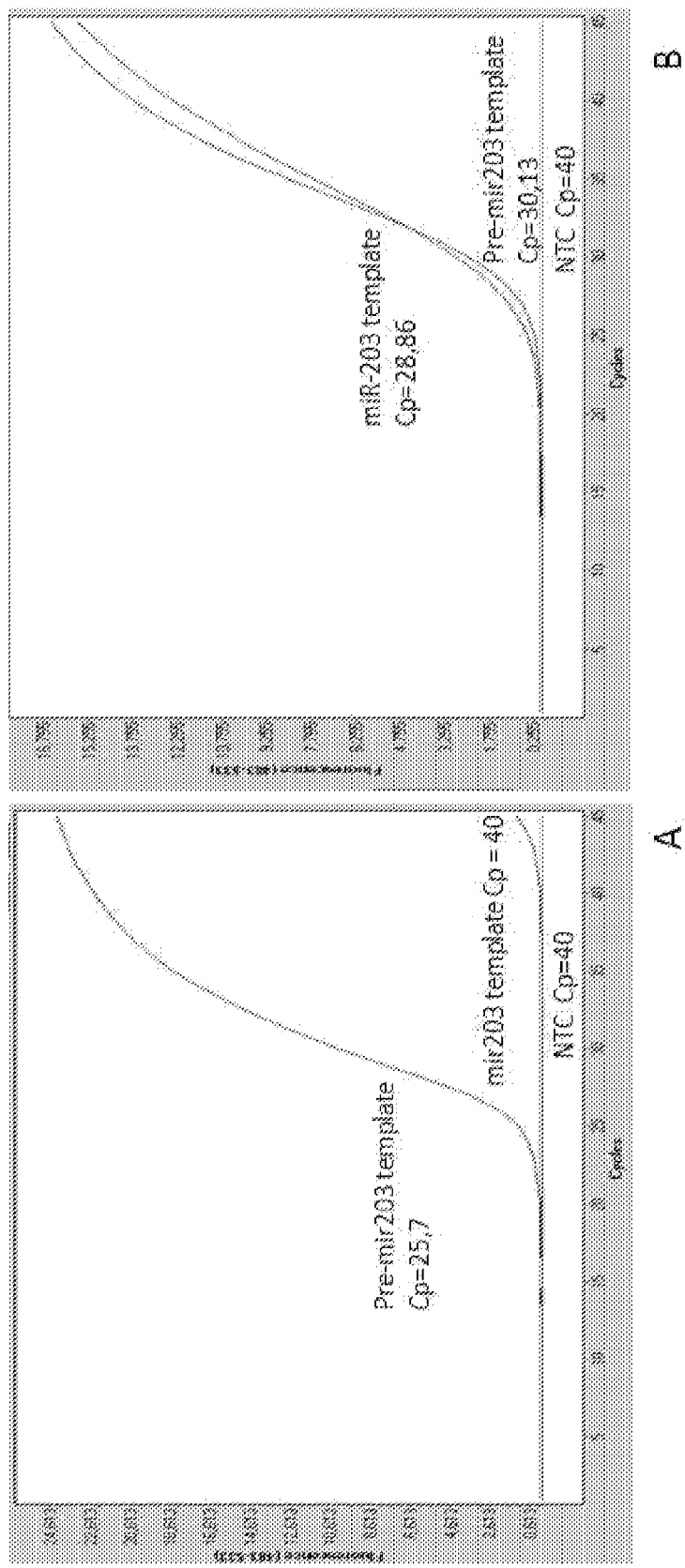

FIG. 6 shows amplification curves of (A) the pre-mir-203 assay on pre-miR-203, miR-203 and non-template controls (NTC). (B) Amplification curves of (A) the miR-203 assay on pre-miR-203, miR-203 and non-template controls (NTC).

Figure 7:
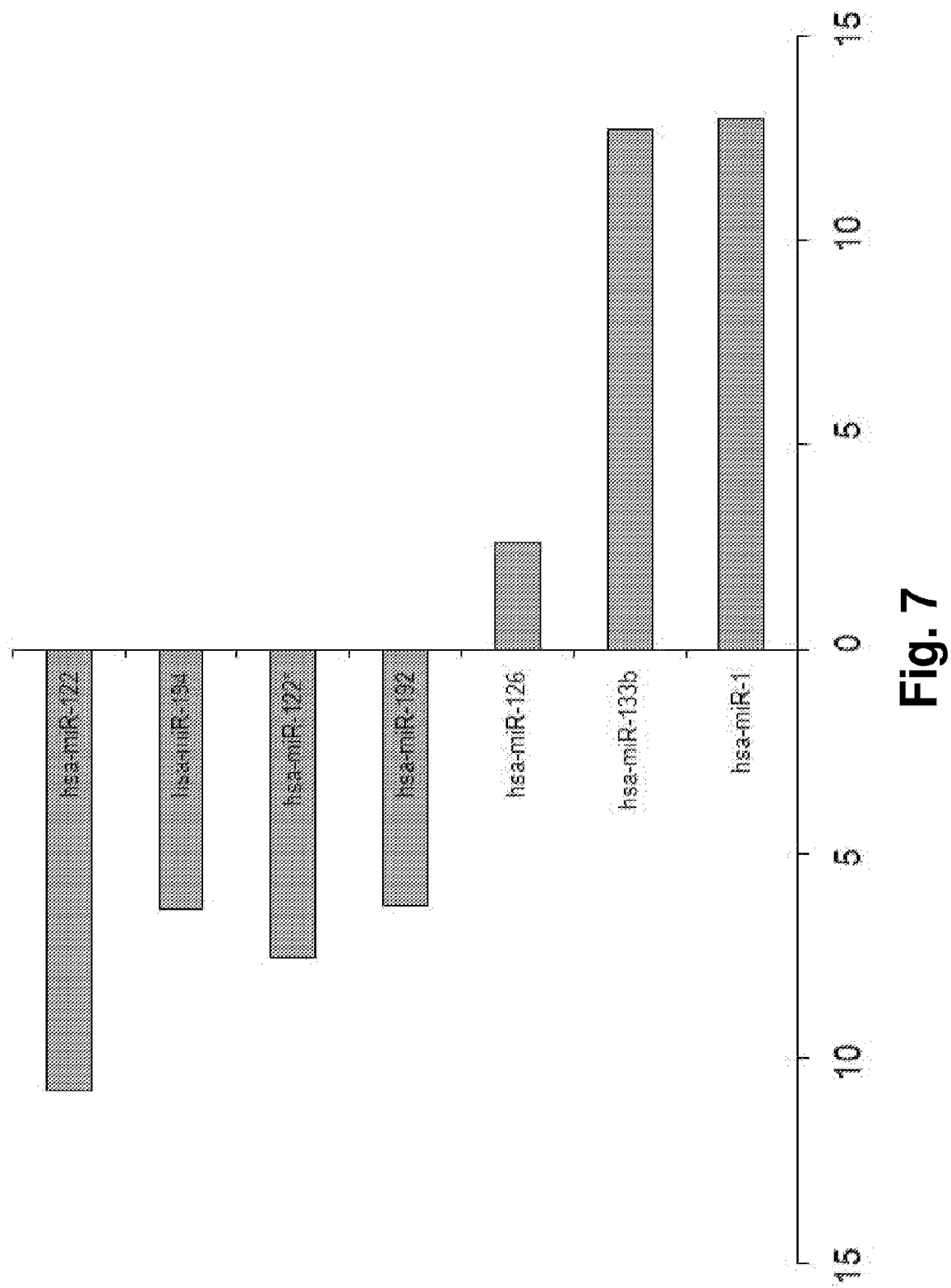

FIG. 7 shows the different expression of a panel of selected miRNA genes in heart and liver. The data is presented as the difference in the crossing point (Cp) value (ΔCp) between heart and liver, see table 15.

Figure 8:
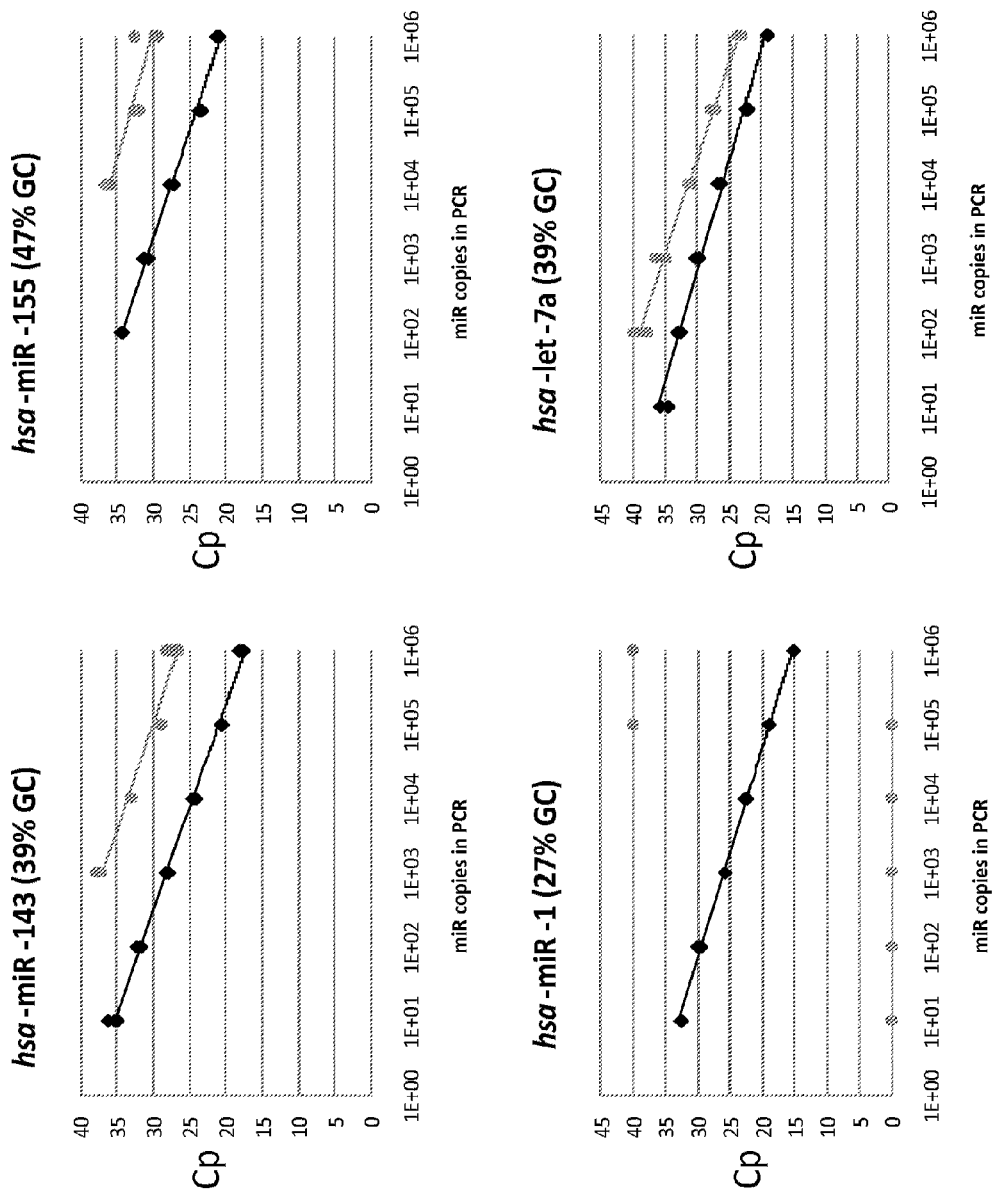

FIG. 8 shows the detection of each of four listed miRs assayed by the present method (black lines with diamonds) and compared with a commercial available method wherein the Reverse Transcription is performed as a one-tube-reaction for all microRNAs present in a sample (gray lines with spheres). The figure presents the crossing point (Cp) values as a function of template concentration. Each value is in triplicate.

DEFINITIONS

"small RNA molecules" refer to tiny RNA molecules; in a living cell such as small "non-coding RNA molecules" i.e. molecules that are not translated into proteins. Non-coding RNA molecules include RNAs such as microRNAs (miRNAs), small interfering RNAs (siRNAs), small nuclear RNAs (snRNAs), small nucleolar RNAs (snoRNAs), small temporal RNAs (stRNAs), antigene RNAs (agRNAs) and piwi-interacting RNAs (piRNAs).

The terms "microRNA", "miRNA" and "miR" are used synonymously and refer to 21-25 nucleotides non-coding RNAs derived from endogenous genes of living organisms such as animals and plants. These socalled mature miRNAs are biologically active and processed from longer hairpin-like precursors termed pre-miRNAs (pre-miRs) having a length of approximately 75 nucleotides. The precursors of pre-miRNAs are pri-miRNAs (pri-miRs) with a length of 500 to 3000 nucleotides. MiRNAs assemble in complexes termed miRNPs and act as major regulators on important biological processes by binding to messenger RNA and interfering with translation efficiency. Target microRNAs of the present invention refer to all known microRNAs, such as microRNAs known from the scientific literature and public databases such as the miRBase database (http://microrna.sanger.ac.uk/) which is the home of microRNA data on the web administrated by the Sanger Institute, UK. The miRBase release 12 is hereby incorporated by reference, including all the mature miRNA and pre-mature miRNA sequences disclosed therein. "microRNA profiling" describes a large-scale analysis in which the expression levels of all microRNAs in a sample such as a tumor sample are determined to build microRNA signatures for a particular disease such as a cancer disease.

"Adding poly-A tails", "Poly-A tailing" and "polyadenylation" refers to the synthesis of a poly(A) tail, a stretch of RNA where all the bases are adenines, at the 3'-termini of an RNA molecule, Polyadenylation is a natural biological process in living organisms, but it can also be carried out in vitro using various polymerases such as commercial available *E. coli* Poly(A) Polymerase I (E-PAP).

"Extension primer" and "RT-primer" refers to an oligonucleotide primer, comprising a recognition sequence, complementary to a sequence in the target deoxyribonucleic and/or ribonucleic acid sequence, e.g. to the 3'-end of the mature microRNA or small noncoding RNA in the target ribonucleic acid sequence, and an anchor sequence essential for subsequent amplification by PCR. The said extension primer is used as an anchored primer in a reverse transcription reaction to generate a primer extension product or cDNA.

A "cDNA" refers to a complementary DNA produced by reverse transcription of an RNA template using a reverse transcriptase enzyme. Any reverse transcriptase can be used to synthesize the cDNA molecules, such as reverse transcriptases derived from moloney murine leukemia virus (M-MuLV) reverse transcriptase, avian myeloblastosis virus (AMV) reverse transcriptase, bovine leukemia virus (BLV) reverse transcriptase, Rous sarcoma virus (RSV) reverse transcriptase and human immunodeficiency virus (HIV) reverse transcriptase.

"Primers" refers to short, chemically synthesized oligonucleotides, usually with a length of about twenty to thirty bases. They are hybridized to a target DNA, which is then copied by a DNA polymerase to produce a complementary DNA strand. A "forward primer" and a "reverse primer" constitute a "PCR primer set" used in PCR, where they hybridise to complementary DNA strands and direct replication towards each other producing the upper-strand and the lower-strand, respectively, leading to an exponential increase in the target DNA segment. The template derived extension of PCR primers can be carried out by any DNA polymerases, such as bacterial thermostable DNA polymerases, including Taq DNA polymerase from *Thermus aquaticus*, Pfu DNA polymerase from *Pyrococcus furiosus*, Vent DNA polymerase from *Thermococcus litoralis* or recombinant DNA polymerases such as Phusion DNA polymerase.

The terms "amplification", "PCR", "PCR reaction" and "PCR amplification", are interchangeable terms used to signify use of a nucleic acid amplification system, which multiplies the target nucleic acids using the polymerase chain reaction (PCR).

"qPCR" and "real-time quantitative PCR" refers to the use of PCR to amplify and simultaneously quantify a targeted DNA molecule. qPCR enables both detection and quantification of the number of copies or relative amount of a specific sequence in a DNA sample, when normalized to DNA input. Amplified DNA is quantified as it accumulates in the reaction in real time after each amplification cycle. Quantification is accomplished using various assay chemistries including fluorescent dyes, such as SYBR® green, that intercalate with double-stranded DNA, and fluorescent reporter oligonucleotide probes such as Taqman probes, that release fluorescence signal during the amplification process.

"qRT-PCR" refers to quantitative reverse transcription polymerase chain reaction in which a cDNA produced in a reverse transcription reaction serves as the initial DNA template for the amplification process, which is then combined with qPCR to quantify low abundance of RNA molecules such as microRNAs in a sample of a particular cell or tissue type. Methods for qPCR and qRT-PCR is described in "A-Z of Quantitative PCR." (Bustin, S A (ed.) International University Line (La Jolla, Calif., USA), 2004) which is hereby incorporated by reference in its entirety.

"Hybridisation" refers to the bonding of two complementary single stranded nucleic acid polymers (such as oligonucleotides), such as RNA, DNA or polymers comprising or consisting of nucleotide analogues (such as LNA oligonucleotides). Hybridisation is highly specific, and may be controlled by regulation of the concentration of salts and temperature. Hybridisation occurs between complementary sequences, but may also occur between sequences which comprise some mismatches. The oligonucleotides used in the methods of the present invention may, therefore be 100% complementary to the target molecule. Alternatively, in one embodiment the oligonucleotides may comprise at least one or two mismatches.

The term "$T_m$" or "melting temperature" of an oligonucleotide is in the present context a measure of the stability of a duplex formed between the oligonucleotide and its perfect complement DNA strand determined at 115 mM Na$^+$, formamide. In general $T_m$ is defined as the temperature at which 50% of the duplexes formed between the oligonucleotide and a complement nucleotide strand are dissociated into single strands. The length and nucleotide composition, such as the sequence of nucleotides and content of G and C nucleotides, of the oligonucleotide are important factors affecting $T_m$. Substitution of the normal A, G, C and T nucleotides with the corresponding LNA molecules in an oligonucleotide increases $T_m$. Similarly, hybridisation conditions defined by salt concentration, oligonucleotide concentration, and the presence of denaturants (such as formamide or DMSO) affects $T_m$. Those skilled in the art of molecular biology know that several useful formulas for calculation of theoretical $T_m$'s have been developed to evaluate the $T_m$ of an oligonucleotide for PCR, Southern and Northern blots, and in situ hybridization. Examples of $T_m$ calculators are OligoCalc (W. A. Kibbe (2007) Nucleic Acids Res Volume 35, Web Server issue W43-W46) and LNA Probe $T_m$ Predictor at http://www.exiqon.com/oligo-tools.

The term "base", as used herein covers the naturally occurring nucleobases adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$-$C^6$)-alkynyl-cytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in Benner et al., U.S. Pat. No. 5,432,272 and Susan M. Freier and Karl-Heinz Altmann, *Nucleic Acid Research*, 25: 4429-4443, 1997. The term "nucleobase" thus includes not only the known purine and pyrimidine heterocycles, but also heterocyclic analogues and tautomers thereof. Further naturally and non naturally occurring nucleobases include those disclosed in U.S. Pat. No. 3,687,808; in chapter 15 by Sanghvi, in *Antisense Research and Application*, Ed. S. T. Crooke and B. Lebleu, CRC Press, 1993; in Englisch, et al., *Angewandte Chemie, International Edition*, 30: 613-722, 1991 (see, especially pages 622 and 623, and in the *Concise Encyclopedia of Polymer Science and Engineering*, J. I. Kroschwitz Ed., John Wiley & Sons, pages 853-359, 1990, Cook, *Anti-Cancer Drug Design* 6: 585-607, 1991, each of which are hereby incorporated by reference in their entirety).

Nucleotides incorporated into oligonucleotides are referred to as nucleotide residues.

The term "nucleosidic base" or "nucleobase analogue" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole or a 5-nitroindole. Other preferred compounds include pyrene and pyridyloxazole derivatives, pyrenyl, pyrenylmethylglycerol derivatives and the like. Other preferred universal bases include, pyrrole, diazole or triazole derivatives, including those universal bases known in the art.

By "locked nucleic acid", "LNA", "LNA monomer" or "LNA molecule" (e.g., an LNA nucleoside or LNA nucleotide) or an LNA oligomer (e.g., an oligonucleotide or nucleic acid) is meant a nucleoside or nucleotide analogue that includes at least one LNA monomer.

To distinguish between LNA and natural occurring nucleotide residues in LNA containing oligonucleotide sequences presented herein, the LNAs are indicated by capital letters, whereas natural occurring nucleotide residues are indicated by lowercase letters: mC denotes LNA methyl cytosine.

LNA monomers as disclosed in PCT Publication WO 99/14226 are in general particularly desirable modified nucleic acids for incorporation into an oligonucleotide of the invention. Additionally, the nucleic acids may be modified at either the 3' and/or 5' end by any type of modification known in the art. For example, either or both ends may be capped with a protecting group, attached to a flexible linking group, attached to a reactive group to aid in attachment to the substrate surface, etc. Desirable LNA monomers and their method of synthesis also are disclosed in WO 98/39352.

Preferred LNA monomers, also referred to as "oxy-LNA" are LNA monomers which include bicyclic compounds as disclosed in PCT Publication WO 03/020739 wherein the bridge between $R^{4'}$ and $R^{2'}$ as shown in formula (I) below together designate —CH$_2$—O— or —CH$_2$—CH$_2$—O—.

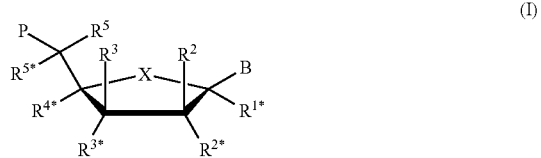

(I)

It is understood that references herein to a nucleic acid unit, nucleic acid residue, LNA monomer, or similar term are inclusive of both individual nucleoside units and nucleotide units and nucleoside units and nucleotide units within an oligonucleotide.

A "modified base" or other similar terms refer to a composition (e.g., a non-naturally occurring nucleotide or nucleosidic base), which can pair with a natural base (e.g., adenine, guanine, cytosine, uracil, and/or thymine) and/or can pair with a non-naturally occurring nucleotide or nucleosidic base. Desirably, the modified base provides a $T_m$ differential of 15, 12, 10, 8, 6, 4, or 2° C. or less as described herein. Exemplary modified bases are described in EP 1 072 679 and WO 97/12896.

The term "chemical moiety" refers to a part of a molecule. "Modified by a chemical moiety" thus refer to a modification of the standard molecular structure by inclusion of an unusual chemical structure. The attachment of said structure can be covalent or non-covalent.

The term "inclusion of a chemical moiety" in an oligonucleotide probe thus refers to attachment of a molecular structure. Such as chemical moiety include but are not limited to covalently and/or non-covalently bound minor groove binders (MGB) and/or intercalating nucleic acids (INA) selected from a group consisting of asymmetric cyanine dyes, DAPI, SYBR® Green I, SYBR® Green II, SYBR® Gold, PicoGreen®, thiazole orange, Hoechst 33342, Ethidium Bromide, 1-O-(1-pyrenylmethyl)glycerol and Hoechst 33258. Other chemical moieties include the modified nucleotides, nucleosidic bases or LNA modified oligonucleotides.

"Oligonucleotide analogue" refers to a nucleic acid binding molecule capable of recognizing a particular target nucleotide sequence. A particular oligonucleotide analogue is peptide nucleic acid (PNA) in which the sugar phosphate backbone of an oligonucleotide is replaced by a protein like backbone. In PNA, nucleotides are attached to the uncharged polyamide backbone yielding a chimeric pseudopeptide-nucleic acid structure, which is homomorphous to nucleic acid forms.

"High affinity nucleotide analogue" or "affinity-enhancing nucleotide analogue" refers to a non-naturally occurring nucleotide analogue that increases the "binding affinity" of an oligonucleotide probe to its complementary recognition sequence when substituted with at least one such high-affinity nucleotide analogue.

As used herein, a probe with an increased "binding affinity" for a recognition sequence compared to a probe which comprises the same sequence but does not comprise a stabilizing nucleotide, refers to a probe for which the association constant ($K_a$) of the probe recognition segment is higher than the association constant of the complementary strands of a double-stranded molecule. In another preferred embodiment, the association constant of the probe recognition segment is higher than the dissociation constant ($K_d$) of the complementary strand of the recognition sequence in the target sequence in a double stranded molecule.

Monomers are referred to as being "complementary" if they contain nucleotides that can form hydrogen bonds according to Watson-Crick base-pairing rules (e.g. G with C, A with T or A with U) or other hydrogen bonding motifs such as for example diaminopurine with T, 5-methyl C with G, 2-thiothymidine with A, inosine with C, pseudoisocytosine with G, etc.

By "oligonucleotide," "oligomer," or "oligo" is meant a successive chain of monomers (e.g., glycosides of heterocyclic bases) connected via internucleoside linkages. The linkage between two successive monomers in the oligo consist of 2 to 4, desirably 3, groups/atoms selected from —CH$_2$—, —O—, —S—, —NR$^H$—, >C=O, >C=NR$^H$, >C=S, —Si(R")$_2$—, —SO—, —S(O)$_2$—, —P(O)$_2$—, —PO(BH$_3$)—, —P(O,S)—, —P(S)$_2$—, —PO(R")—, —PO(OCH$_3$)—, and —PO(NHR$^H$)—, where R$^H$ is selected from hydrogen and C$_{1-4}$-alkyl, and R" is selected from C$_{1-6}$-alkyl and phenyl. Illustrative examples of such linkages are —CH$_2$—CH$_2$—CH$_2$—, —CH$_2$—CO—CH$_2$—, —CH$_2$—CHOH—CH$_2$—, —O—CH$_2$—O—, —O—CH$_2$—CH$_2$—, —O—CH$_2$—CH= (including R$^5$ (see formula I) when used as a linkage to a succeeding monomer), —CH$_2$—CH$_2$—O—, —NR$^H$—CH$_2$—CH$_2$—, —CH$_2$—CH$_2$—NR$^H$—, —CH$_2$—NR$^H$—CH$_2$—, —O—CH$_2$—CH$_2$—NR$^H$—, —NR$^H$—CO—O—, —NR$^H$—CO—NR$^H$—, —NR$^H$—CS—NR$^H$—, —NR$^H$—C(=NR$^H$)—NR$^H$—, —NR$^H$—CO—CH$_2$—NR$^H$—, —O—CO—O—, —O—CO—CH$_2$—O—, —O—CH$_2$—CO—O—, —CH$_2$—CO—NR$^H$—, —O—CO—NR$^H$—, —NR$^H$—CO—CH$_2$—, —O—CH$_2$—CO—NR$^H$—, —O—CH$_2$—CH$_2$—NR$^H$—, —CH=N—O—, —CH$_2$—NR$^H$—O—, —CH$_2$—O—N= (including R$^5$ when used as a linkage to a succeeding monomer), —CH$_2$—O—NR$^H$—, —CO—NR$^H$—CH$_2$—, —CH$_2$—NR$^H$—O—, —CH$_2$—NR$^H$—CO—, —O—NR$^H$—CH$_2$—, —O—NR$^H$—, —O—CH$_2$—S—, —S—CH$_2$—O—, —CH$_2$—CH$_2$—S—, —O—CH$_2$—CH$_2$—S—, —S—CH$_2$—CH= (including R$^5$ when used as a linkage to a succeeding monomer), —S—CH$_2$—CH$_2$—, —S—CH$_2$—CH$_2$—O—, —S—CH$_2$—CH$_2$—S—, —CH$_2$—S—CH$_2$—, —CH$_2$—SO—CH$_2$—, —CH$_2$—SO$_2$—CH$_2$—, —O—SO—O—, —O—S(O)$_2$—O—, —O—S(O)$_2$—CH$_2$—, —O—S(O)$_2$—NR$^H$—, —NR$^H$—S(O)$_2$—CH$_2$—, —O—S(O)$_2$—CH$_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(OCH$_2$CH$_2$S—R)—O—, —O—PO(BH$_3$)—O—, —O—PO(NHR$^N$)—O—, —O—P(O)$_2$—NR$^H$—, —NR$^H$—P(O)$_2$—O—, —O—P(O,NR$^H$)—O—, —CH$_2$—P(O)$_2$—O—, —O—P(O)$_2$—CH$_2$—, and —O—Si(R")$_2$—O—; among which —CH$_2$—CO—NR$^H$—, —CH$_2$—NR$^H$—O—, —S—CH$_2$—O—, —O—P(O)$_2$—O—, —O—P(O,S)—O—, —O—P(S)$_2$—O—, —NR$^H$—P(O)$_2$—O—, —O—P(O,NR$^H$)—O—, —O—PO(R")—O—, —O—PO(CH$_3$)—O—, and —O—PO(NHR$^N$)—O—, where R$^H$ is selected form hydrogen and C$_{1-4}$-alkyl, and R" is selected from C$_{1-6}$-alkyl and phenyl, are especially desirable. Further illustrative examples are given in Mesmaeker et. al., Current Opinion in Structural Biology 1995, 5, 343-355 and Susan M. Freier and Karl-Heinz Altmann, Nucleic Acids Research, 1997, vol 25, pp 442.9-4443. The left-hand side of the internucleoside linkage is bound to the 5-membered ring as substituent P* at the 3'-position, whereas the right-hand side is bound to the 5'-position of a preceding monomer.

The term "succeeding monomer" relates to the neighbouring monomer in the 5'-terminal direction and the "preceding monomer" relates to the neighbouring monomer in the 3'-terminal direction. It should be noted that whereas the natural synthesis of DNA and RNA proceed in the direction 5' to 3', many chemical synthesis-schemes proceed in the direction of 3' to 5'.

When performing quantitative PCR, the cycle at which the fluorescence from a sample crosses the threshold is called the "cycle threshold" or Ct. Ct is used for quantification of a template.

The "crossing point" or Cp value is a slightly different, but related value that can be used for quantification of a template somewhat similar to the use of Ct. The LightCycler® 480 Software calculates the second derivatives of entire amplification curves and determines where this value is at its maximum. This value (crossing point, Cp) represents the cycle at which the increase of fluorescence is highest and where the logarithmic phase of a PCR begins. Both terms Ct and Cp are further explained in Bustin, S A (ed.) "A-Z of Quantitative PCR." International University Line (La Jolla, Calif., USA), 2004, which is included herein by reference.

Suitably, the "target" or "target nucleic acid" or "target ribonucleic acid" refers to any relevant nucleic acid of a single specific sequence, e.g., a biological nucleic acid, e.g., derived from a subject or human being. Within the context of the oligonucleotides and detection probes used in the invention to detect miRNAs, the "target" is a human miRNA or precursor thereof, or in one embodiment, a molecule which retains the genetic sequence information contained therein—such as all or (a sufficient) part of the sequence of nucleotides or reverse complement thereof.

"Target sequence" refers to a specific nucleic acid sequence (or corresponding nucleobase sequence) within any target nucleic acid.

The term "primer design" refers to methods such as those provided below. The primer design is an systematic approach used for designing the sequence of nucleotides in forward and reverse primers thus ensuring probe specificity and binding efficiency to target microRNAs. The following rules have been used for design of primers for miR-specific qPCR:
Forward Primer Design:

Preferably, the forward primers are designed to be identical of from 12 to 18 bases of the 5' end of the miR sequence. Preferably, the Tm of the forward primers should be in the range of between 55° C. and 65° C., however, a Tm below 55° C. and above 65° C. may also be acceptable. To ensure that the Tm of the primers preferably is in the range of between 55° C. and 65° C., one or more LNA monomers may be inserted into the sequence substituting the natural nucleotide. An artificial nucleotide sequence may also be added to the 5'-end of the forward primer to make certain that the Tm is in the range of between 55° C. and 65° C.
Reverse Primer Design:

The reverse primer is according to formula II:

$$R^3\text{-}(T)_x\text{-}R^4 \qquad (II)$$

wherein R$^3$ is a 5'-end nucleotide sequence, (T)$_x$ is a central part of x consecutive thymine residues in the amount of x, wherein x is an integer of from 1 to 100, and R$^4$ is a 3'-end nucleotide sequence that specifically hybridizes to a part of a microRNA molecule.

R$^4$ is preferably a nucleotide sequence of from 1 to 10 nucleotides designed from the 3'-end of a specific miRNA. R$^4$ is able to hybridize specifically to the DNA strand (i.e. the upper-strand) produced by extension of the corresponding miRNA specific forward primer. To ensure miRNA specificity and make certain that the T$_m$ of the primer preferably is in the range of between 55° C. and 65° C., one or more LNA monomer may be inserted into the R$^4$ sequence substituting the corresponding natural nucleotide.

The (T)$_x$ central part is preferably a stretch of approximately 15 consecutive thymine nucleotide residues that hybridizes to the poly-A-tail part of the DNA strand produced from the corresponding miRNA specific forward primer.

The R$^3$ sequence of the reverse primer typically has a length of form 1 to 20 nucleotides. For example R$^3$ can be 17 nucleotides long, 8, 7 or 6 nucleotides long or even only one nucleotide long. In certain embodiments of the present invention, the R$^3$ sequence is 5'-TGACACGGAGGTACTAG-3' (SEQ ID NO 3). The length of the R$^3$ sequence may be reduced from the 5'-end to adjust the T$_m$ of the reverse primer to the preferable range of between 55° C. and 65° C. The R$^3$ sequence is identical to or at least has overlap to part of the R$^1$ sequence (formula (III)) of the extension primer.

The procedure for designing the reverse primer is described below.
A. Design a number of primers that fulfil the following conditions:
  1) Delete all adenine residues from 3'-end of miR nucleotide sequence. They will form part of the poly-A tail.
  2) After deleting adenine residues start with reverse complement to 3' end base of the miR and continue until one base overlap with forward primer.
  3) Delete one base from the 3' end of the reverse primer if the sequence is a cytosine residue and the 3' end of the forward primer is a guanine residue.
  4) Delete one base from the 3' end of the primer if the sequence is a guanine residue and the 3' end of the forward primer is a cytosine residue.

5) Delete one base from the 3' end of the primer if the last two bases are overlapping with the last two bases of the forward primer (from the 3' end).
6) Repeat this process until the conditions are fulfilled.
7) If no primer fulfils the conditions disregard rules #2 and 3 and allow two bases overlap (but not more) for sequences ending with AA, AT, TA or TT,
8) If no primer fulfils the conditions try another forward primer design.

B. Choose the longest reverse primer that fulfils the following conditions:
1) At least four bases long.
2) Less than five cytosine residues and guanine residues in the last six bases at the 3' end of the primer.
3) Less than four cytosine residues and guanine residues in the last five bases at the 3' end of the primer except if the last or second last base is an adenine residue or thymine residue.
4) If possible not more than two adenine residues or thymine residues in the 3' end.
5) If no primer fulfils the conditions try another forward primer design.

C. Optionally insert one LNA monomer according to the following rules:
1) Insert LNA at first cytosine residue or guanine residue from 5' end of the $R^4$ part of the reverse primer.
2) No LNA in sequences with three or more consecutive cytosine residues or guanine residues.
3) LNA should be in position four or higher from the 3' end of the primer.
4) If the conditions cannot be fulfilled insert LNA at first adenine residue or thymine residue from 5' end of the $R^4$ part of the reverse primer.
5) LNA should be in position four or higher from the 3' end of the primer.
6) If the conditions cannot be fulfilled insert LNA-thymine (LNA-T) at 5' end of the $R^4$ part of the primer.

D. Tailing:
Add a sequence of the formula $R^3$-$(T)_x$ to the 5' end of the reverse primer. In certain embodiments of the present invention the nucleotide sequence:
5'-TGACACGGAGGTACTAGTTTTTTTTTTTTTTT-3' (SEQ ID NO 4) is added at the 5' end of the reverse primer.
If an LNA-T was added to the miR-specific part of the reverse primer (step C6) delete one thymine residue from the tail as there should never be more than 15 consecutive thymine residues.
Eventually, nucleotides are removed from the 5'-end of the reverse primer to fine-tune the $T_m$ of the primer.

"Sample" of RNA refers to RNA comprising compositions obtained from cells, tissues or fluids from an organism according to conventional procedures described e.g. in RNA Isolation and Characterization Protocols (Rapley, Ralph; Manning, David L. (Eds.) 1998) known to the skilled artesian or by using commercial kits such as miRNeasy (QIAGEN GmbH, Hilden, Germany)) or miRVana (Ambion Inc., Austin, Tex., US). Sources for isolation of RNA fractions are samples of cells, or tissue or fluid isolated from an organism or organisms, including but not limited to, for example, skin, plasma, serum, spinal fluid, lymph fluid, synovial fluid, urine, tears, blood cells, organs, tumours, and also to samples of in vitro cell culture constituents (including but not limited to conditioned medium resulting from the growth of cells in cell culture medium, recombinant cells and cell components), "Sample" may also refer to cells or fluids that can be used directly in a qRT-PCR process without previous enrichment of the RNA fraction or even RNA comprising compositions comprising artificially synthesised RNA.

Cells or cell types also refer to any cells of Eukaryote, Prokaryote and Archaea origin.

A "living organism" refers to a living entity, including but not limited to, for example, human, mouse, rat, *Drosophila, C. elegans*, yeast, *Arabidopsis thaliana*, maize, rice, zebra fish, primates, domestic animals, etc.

DETAILED DESCRIPTION OF THE PREFERRED EMBODIMENT

Figure 1:
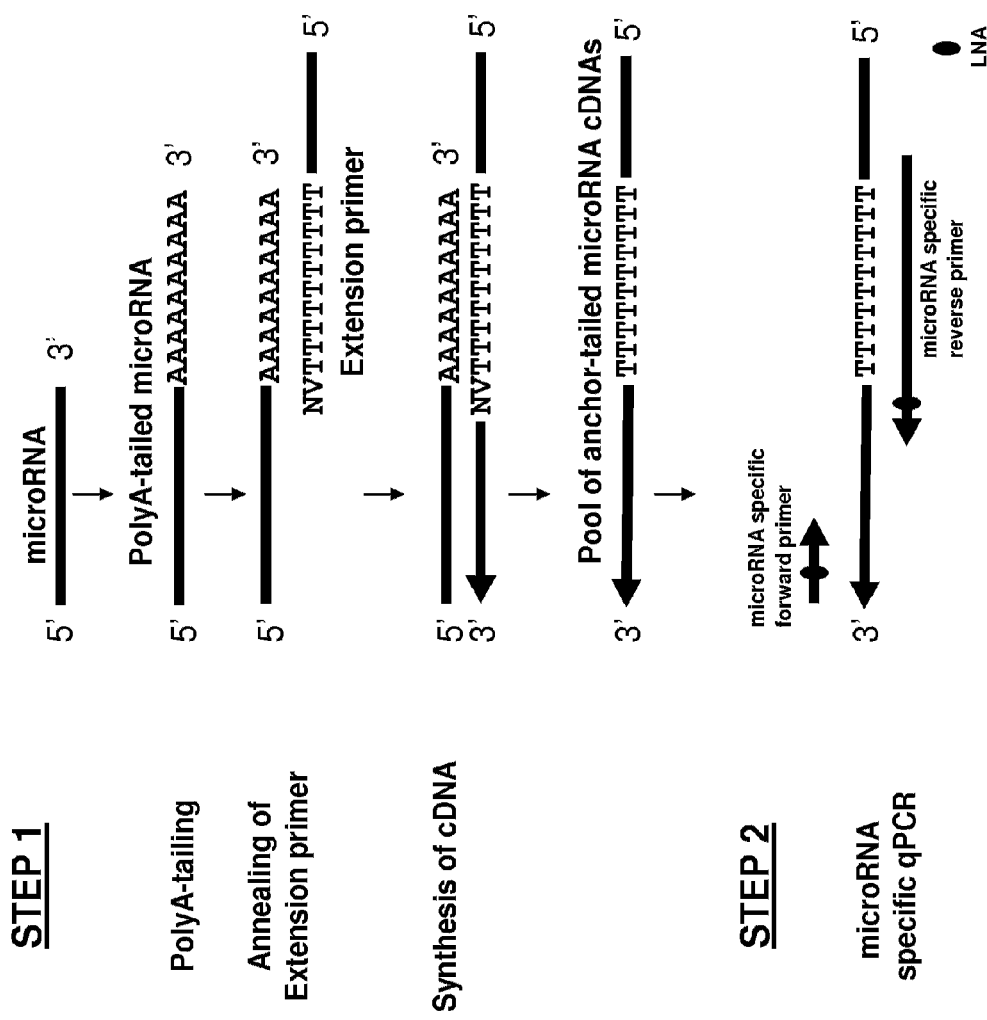

Detailed Outline of the qRT-PCR Reaction and the Primers Involved:

The present invention provides methods for amplification of microRNA molecules in a sample, the method comprising the steps described schematically in FIG. 1, and comprise:
(a) adding poly-A tails to a population of RNA molecules in a sample;
(b) producing cDNA molecules of the poly-A-tailed RNA molecules using an extension primer in a reverse transcription reaction; and
(c) amplifying the cDNA molecules by PCR using a forward primer and a reverse primer both of which are specific for said RNA molecule.

When performing the method in practice step (a) and (b) is typically performed as one concerted reaction which is universal for all RNAs to be analysed—hence its nickname: "Universal RT". The advantage of only one first-strand cDNA synthesis reaction (or RT reaction) to be used as template for multiple real-time PCR assays is that it saves precious sample, reduces technical variation and reduces time spent in the laboratory.

During step (c) of the method individual (or groups of individual) RNAs are specifically PCR amplified using specific forward and reverse primers. Typically the primers are optimised by introducing one or more LNA nucleotide analogues into the sequence of the primers, and typically the PCR is quantitative Real-Time PCR. As can be seen from the examples the method result in 1) uniquely specific assays that enable discrimination between highly related RNA sequences and 2) an extremely low background which enables accurate quantitation of very low RNA levels.

The method has been extensively used to quantify small RNAs. In a preferred embodiment the small RNA, comprises small non-coding RNAs such as short inferring RNAs (siRNAs), mature microRNAs and pre-microRNAs. Also larger RNAs, e.g. precursors of pre-microRNAs the pri-miRNAs (pri-miRs) and mRNAs may be assessed by method.

Most preferably the small RNA is a microRNA.

The extension primer may be of a length in the range from 10 to 100 nucleotides, such as a length in the range from 15 to 45 nucleotides. Preferably, the extension primer has a length of 20, 21, 22, 23, 24, 25, 26, 27, 28, 29 or 30 nucleotides.

In a preferred embodiment, the extension primer is of the formula III.

wherein $R^1$ is a 5'-end nucleotide sequence, $(T)_y$ is a central part of consecutive thymine residues in the amount of y, wherein y is an integer of from 1 to 100, and $R^2$ is a 3'-end nucleotide sequence.

Typically, the 5'-end part $R^1$ is a nucleotide sequence with a length of from 1 to 30 nucleotides. For example the $R^1$ sequence may be 6, 7, 8, 9, or 10 nucleotides long. The $R^1$ sequence includes east a hybridisation sequence for the $R^3$ sequence in the reverse primer of the formula II (see below) to be used in the subsequent miRNA-specific qPCR.

Preferably, y in formula III is in the interval of from 5 to 50, more preferably y is in the interval of from 5 to 21. For example y is 12, 13, 14, 15, 16, 17 or 18. Most preferably y is 15.

In one especially preferred embodiment y of formula (III) equals x of formula (II).

in a preferred embodiment, $R^2$ is a degenerated anchor sequence motif VN, comprising the two 3'-end terminal nucleotide residues, wherein V designate a selection of residues comprising bases which can base pair to all but one of the natural bases (e.g. base pair to guanine, cytosine, uracil and thymine but not to adenine), typically V designate that the base in any primer molecule is a base randomly selected between adenine, guanine and cytosine and wherein N designate a base which can base pair to any of the natural bases (e.g. adenine, guanine, cytosine, uracil and thymine), typically N may be a base randomly selected between adenine, guanine, cytosine or thymine residue.

In another preferred embodiment $R^2$ is a degenerated sequence motif VN, comprising the three 3'-end terminal nucleotide residues, wherein V designate a selection of residues comprising bases which can base pair to all but one of the natural bases (e.g. base pair to guanine, cytosine, uracil and thymine but not to adenine), typically V designate that the base is a base randomly selected between adenine, guanine and cytosine and wherein N designate a base which can base pair to any of the natural bases (e.g. adenine, guanine, cytosine, uracil and thymine), typically N may be a base randomly selected between adenine, guanine, cytosine or thymine residue.

In a preferable embodiment, the extension primer comprises at least one LNA.

In a certain embodiment of the present invention the extension primer has the sequence 5'-GGTAC-TAGTTTTTTTTTTTTTT-3' (SEQ ID NO 5).

Preferably, the forward primer has a length in the range of from 10 to 100 nucleotides, such as 12 to 22 or 13 to 20 or 14, 15, 16, 17, 18 or 19 nucleotides. See table 18 for specific embodiments.

The forward primer may comprise one, two or even more LNAs.

In a preferred embodiment, the nucleotide sequence of the forward primer is designed to specifically hybridize to the complement DNA molecule of a specific microRNA molecule using the primer design rules described in the definition of "primer design" (see DEFINITIONS section)

Preferably, the reverse primer is of the formula II:

$$R^3-(T)_x-R^4 \qquad (II)$$

wherein $R^3$ is a 5'-end nucleotide sequence $(T)_x$ is a central part of consecutive thymine nucleotides in the amount of x, wherein x is an integer of from 1 to 100, and $R^4$ is a 3'-end nucleotide sequence that specifically hybridizes to a nucleotide sequence of a target RNA molecule.

Preferably, the 5'-end nucleotide sequence $R^3$ of the reverse primer of formula II is a nucleotide sequence with a length of from 1 to 30 nucleotides.

Preferably, x in formula II is in the interval of from 5 to 50, more preferably x in the interval of from 5 to 21. For example x is 12, 13, 14, 15, 16, 17 or 18. Most preferably x is 15.

In one especially preferred embodiment x of formula (II) equals y of formula (III).

In a preferred embodiment, the 3'-end nucleotide sequence $R^4$ of the reverse primer of formula II has a length in the range of from 1 to 10 nucleotides.

As illustrated in example 2 LNA has a profound effect. Accordingly, in a preferred embodiment, the 3'-end part, $R^4$, of the reverse primer of formula II comprises at least one LNA. More preferably, the 3'-end part, $R^4$, of the reverse primer of formula II contains only one LNA. In a particularly preferred embodiment the LNA is situated in the 5' position or the position adjacent to the 5' position of the $R^4$ part of the reverse primer.

In a preferred embodiment the nucleotide sequence of the reverse primer is designed to specifically hybridize to a specific microRNA molecule using the primer design rules described in the definition or "primer design" (see DEFINITIONS section)

Design of Primers

The invention also provides methods for designing the nucleotide sequence of the forward primers and the reverse primers used in the invention. Systematic approaches and experimental evaluation of the primers are presented in the EXAMPLES 3 section.

Examples of Applications of the Present Invention

The present invention is useful for amplification and quantification of small RNA molecules such as microRNAs or siRNA's in various cells or tissues originating from humans or other organisms as described in EXAMPLES 5 and 9. As illustrated in example 10 the present method is superior with respect to sensitivity and specificity when compared with a somewhat similar single tube cDNA synthesis approach which is commercially available.

Thus one aspect of the invention is a method for measuring the amount of at met microRNA in a sample from a living organism, the method comprising the steps of:
  a) amplifying the target microRNA according to the method of any one of claims 1 to 28
  b) measuring the amount of the amplified DNA molecules.

The amount of the amplified DNA molecules is typically measured using fluorescence-based quantitative real-time PCR by e.g. monitoring SYBR® green fluorescence as a function of PCR cycle number.

Accordingly, the present invention can be used as a tool for microRNA profiling of different cell and tissue types within a living organism. Thus, the number of specific microRNAs and the amounts of specific microRNAs present in different cell and tissue types can be determined using the present invention. Similarly, the invention can be used to discriminate between the levels of mature microRNAs, pre-microRNAs and pri-microRNAs in different cell and tissue types by using appropriate primers targeting the mature microRNA or its precursors (see FIG. 5).

In another aspect, the present invention can be used as a tool for microRNA profiling of patients suffering from various diseases such as cancer. By way of example, the microRNAomes of various cancer tissues can be established using the invention.

In yet another aspect the present invention can be used for diagnosis of various diseases such as cancer by measuring microRNA expression in tissues and body fluids from normal individuals and from individuals having a disease, and subsequently analyse for differences in the microRNA profiles.

In another embodiment the present invention may be used for measuring changes in the amount of specific microRNAs in response to treatment of a disease affected individual by means of pharmaceuticals, such as chemotherapeutical agents, and by means of surgery.

In another embodiment the present invention may be used for measuring specific predictive microRNA biomarkers that correlate with re-currence free survival of patients having a disease, such as a cancer disease.

Due to its simplicity: one "universal-RT" step and one discriminatory PCR step, the present invention is also suitable for high-throughput methods on robot platforms directed to the quantification of a single microRNA or a collection of microRNAs. Thus, the method is particularly suitable for multiple subsequent PCR reactions of individual microRNAs described in EXAMPLE 5, 9 and 10.

In a certain embodiment the method of the invention may be used to quantitatively determine the amount of mature microRNA in a sample without interference from the corresponding pre-miR, and vice versa the amount of a pre-miR can be determined without interference from the mature microRNA as described in EXAMPLES 6, 7 and 8.

In another embodiment the method of the invention may be used for discrimination between targets with single nucleotide differences as described in EXAMPLE 4.

In another aspect, the present invention provides kits for detecting at least one target microRNA, the kits comprising one or more primer sets specific for the detection of a target microRNA, each primer set comprising firstly, a universal extension primer for producing a cDNA molecule complementary to a target microRNA, and secondly, a PCR primer set comprising a forward primer specific for the 5'-end of the target miRNA and a reverse primer specific for the 3'-end of the target miRNA for amplifying the cDNA molecule.

Accordingly in one aspect the invention a kit for detecting at least one target RNA is provided. The kit comprises at least one primer set specific for the detection of a target RNA, said primer set comprises:

a) an extension primer of formula I: $R^1-(T)_y-R^2$ (III)
wherein $R^1$ is a 5'-end nucleotide sequence, $(T)_y$ is a central part of consecutive thymine residues in the amount of y, wherein y is an integer of from 1 to 100, and $R^2$ is a 3'-end nucleotide sequence.

b) a reverse primer of formula II: $R^3-(T)_x-R^4$ (II)
wherein $R^3$ is a 5'-end nucleotide sequence, $(T)_x$ is a central part of consecutive thymine residues in the amount of x, wherein x is an integer of from 1 to 100, and $R^4$ is a 3'-end nucleotide sequence that specifically hybridizes to a nucleotide sequence of a target RNA molecule, and c) a forward primer In one embodiment the kit is designed for detecting at least one mammalian target microRNA comprising at least one primer set specific for the detection of a target microRNA.

Preferably, the extension, the reverse and the forward primers are designed following the design rules given in the"primer design"-part of the DEFINITIONS section and elsewhere and forward and reverse primers which includes at least one LNA molecule are especially preferred embodiments.

A non-limiting example of an extension primer is shown as SEQ ID NO 5.

Forward and reverse primers included in the kit may be designed to detect any mammalian target microRNA in accordance with the methods described herein. Non-limiting examples of forward and reverse primers are listed in TABLE 16.

In certain embodiments, the kit includes multiple primer sets that may be used to detect various mammalian microRNA targets, such as two microRNA targets up to several hundred microRNA targets.

A kit of the invention may also provide an array of primers delivered in microtiter qPCR plates such as 96, 768, 369, 1536 or even 3456-well microtiter qPCR plates suitable for robot handling as indicated in EXAMPLE 9.

A kit of the invention may also include reagents required for the poly-A-tailing, primer extension and PCR reactions, such as buffers, salts, reducing agents, deoxy nucleoside triphosphates, nucleoside triphosphates, and enzymes. A detection reagent for the qPCR such as SYBR® green may also be included. Similarly a kit for RNA isolation may also be included.

A further aspect of the invention is a high-throughput method for measuring the amount of specific target microRNAs in a sample from a living organism by using the method of the present invention and integrating an automated wherein the combined poly-A-tailing and reverse transcription reaction is aliquoted into individual wells of a microliter plate containing microRNA specific primer sets of forward and reverse primers, resulting in the steps of:

a) adding poly-A tails to a population of small RNA molecules in a sample and producing cDNA molecules of the poly-A-tailed small RNA molecules using an extension primer in a reverse transcription reaction; and b) pipetting aliquots of the combined poly-A-tailing and reverse transcription reaction into individual wells of a microtiter plate c) amplifying specific target microRNAs in individual wells of a microtiter plate containing microRNA specific primer sets d) measuring the amount of specific microRNA molecules in individual wells.

being performed in a fashion compatible with a high-throughput experimental set-up. Such a set-up will typically comprise one or more pipetting robots.

EXAMPLES

Example 1

Production of Specific DNA Molecules Using miR-specific qPCR

In this example hsa-miR-197 was amplified from a human RNA sample using the miR specific quantitative reverse transcription polymerase chain reaction (qRT-PCR) of this invention.

Mixed on Ice:
1 µl 10× Poly(A) polymerase buffer (New England Biolabs)
1 µl 1 mM ATP
1 µl 10 µM RT-primer (=extension primer) (L2TA: 5'-gg-tactagtttttttttttttttvn (SEQ ID NO 5), v designates cytosine, guanine and adenine residues, n designates cytosine, guanine, adenine and thymine residues)).
1 µl mix of 1 mM dATP, 1 mM dCTP, 1 mM dGTP, 1 mM dTTP
0.5 µl (200 U/µl) MuLV reverse transcriptase (New England Biolabs Inc, Ipswich, Mass., US)
0.2 µl (5 U/µl) Poly(A) polymerase (New England Biolabs)
1 µl RNA sample (total human RNA sample=100 ng of a mixture of 25 ng human heart RNA, 25 ng human brain RNA, 25 ng human liver RNA and 25 ng human lung RNA all from Ambion, Austin, Tex., US. Synthetic templates were prepared in 10 ng/µl phage MS2 RNA in TE, approximately $10^7$ copies are added to the reaction. Synthetic template is obtained from Integrated DNA technologies Inc., Coralville, Iowa, US.)
Water to 10 µl
Negative controls: water control and a total human RNA control without PolyA Polymerase in the RT reaction.

The mixture was incubated at 42° C., 1 hour followed by 95° C., 5 minutes.

For qPCR 1 µl or less of the polyA-tailing/RT reaction (step 1 on FIG. 1) was used for each PCR reaction with gene-specific forward and reverse primers for hsa-miR-197; forward primer 5' ttmCaccaccttctcca (SEQ ID NO 1) and the reverse primer 5'-cttttttttttttttttGctgggt (SEQ ID NO 2) (in the nucleotide sequences lower case designates a natural occurring nucleotide, upper case designates LNA, mC denotes LNA methyl cytosine).

Real-time PCR was done on a ABI 7500® thermocycler (Applied Biosystems Inc, Foster City, Calif., US) by monitoring SYBR® green fluorescence as a function of PCR cycle number. A typical PCR reaction mixture contained:
- 10 µl 2×PCR mastermix (Roche cat#04 673 484 001, Roche Diagnostics A/S; Hvidovre, Denmark)
- 1 µl or less of the RT reaction
- 1 µl TE buffer with 2.5 µM miR-specific forward primer and 2.5 µM miR-specific reverse primer (TE buffer: 10 mM Tris/HCl (pH 8.0), 1 mM EDTA).
- Water to 20 µl.

The mixture was incubated at 95° C. for 10 min followed 40 cycles of 95° C. for 5 sec; 60° C. for 60 sec with measurement of the fluorescence.

Amplification of the correct product was measured by comparing the melting curve profile of the PCR product to the melting curve profile of a PCR product obtained by amplification of a synthetic template (FIG. 2). No signal was obtained with the negative controls. The experiment shows that the same and correct hsa-miR-197 PCR product was obtained both using the total human RNA sample and a c hsa-miR-197 as template in step 1.

Example 2

Effect of LNA in the Reverse Primer

The effect of different designs of miR-specific PCR primers of step 2 can be tested on artificial DNA templates with the same sequence as the product of the reverse transcription reaction. An important advantage of using an artificial DNA template for PCR is that experimental variations in the efficiency of the reverse transcription step are eliminated.

Hsa-let-7a DNA Template:

(SEQ ID NO 6)
5'-tgcggtgacacggaggtac-
tagttttttttttttttttaactatacaacc tactacctca-3'

Salmon DNA: 2 ng/µl in TE buffer
miR-specific Forward Primer:
F7a: 5'-tGaGgtagtaggttg (SEQ ID NO 7) (lower case designates a natural occurring nucleotide, upper case designates LNA).

miR-specific Reverse Primers:

r7a.2:
(SEQ ID NO 8)
5'-cggtgacacggagatactagttttttttttttttttaactata r7a.7:
(SEQ ID NO 9)
5'-cggtgacacggaggtactagttttttttttttttttaamCaata A PCR mix was prepared:
550 µl 2×PCR mastermix (Roche cat#04 673 484 001)
440 µl water, and as described i tab 1.

TABLE 1

Four PCR reactions were prepared:

| Sample | Template | 10 µM forward primer | 10 µM reverse primer | PCR Mix |
|---|---|---|---|---|
| #1 | 1 µl salmon DNA | 0.5 µl F7a | 0.5 µl r7a.2 | 18 µl |
| #2 | 10000 copies of hsa-let-7a DNA template in salmon DNA | 0.5 µl F7a | 0.5 µl r7a.2 | 18 µl |
| #3 | 1 µl salmon DNA | 0.5 µl F7a | 0.5 µl r7a.7 | 18 µl |
| #4 | 10000 copies of hsa-let-7a DNA template in salmon DNA | 0.5 µl F7a | 0.5 µl r7a.7 | 18 µl |

Real-time PCR was carried out on a ABI 7500 ® thermocycler by monitoring SYBR ® green fluorescence as a function of PCR cycle number.

The mixture was incubated at 95° C. for 10 min followed by 40 cycles of 95° C. for 5 sec; 60° C. for 60 sec with measurement of the fluorescence.

Figure 3:
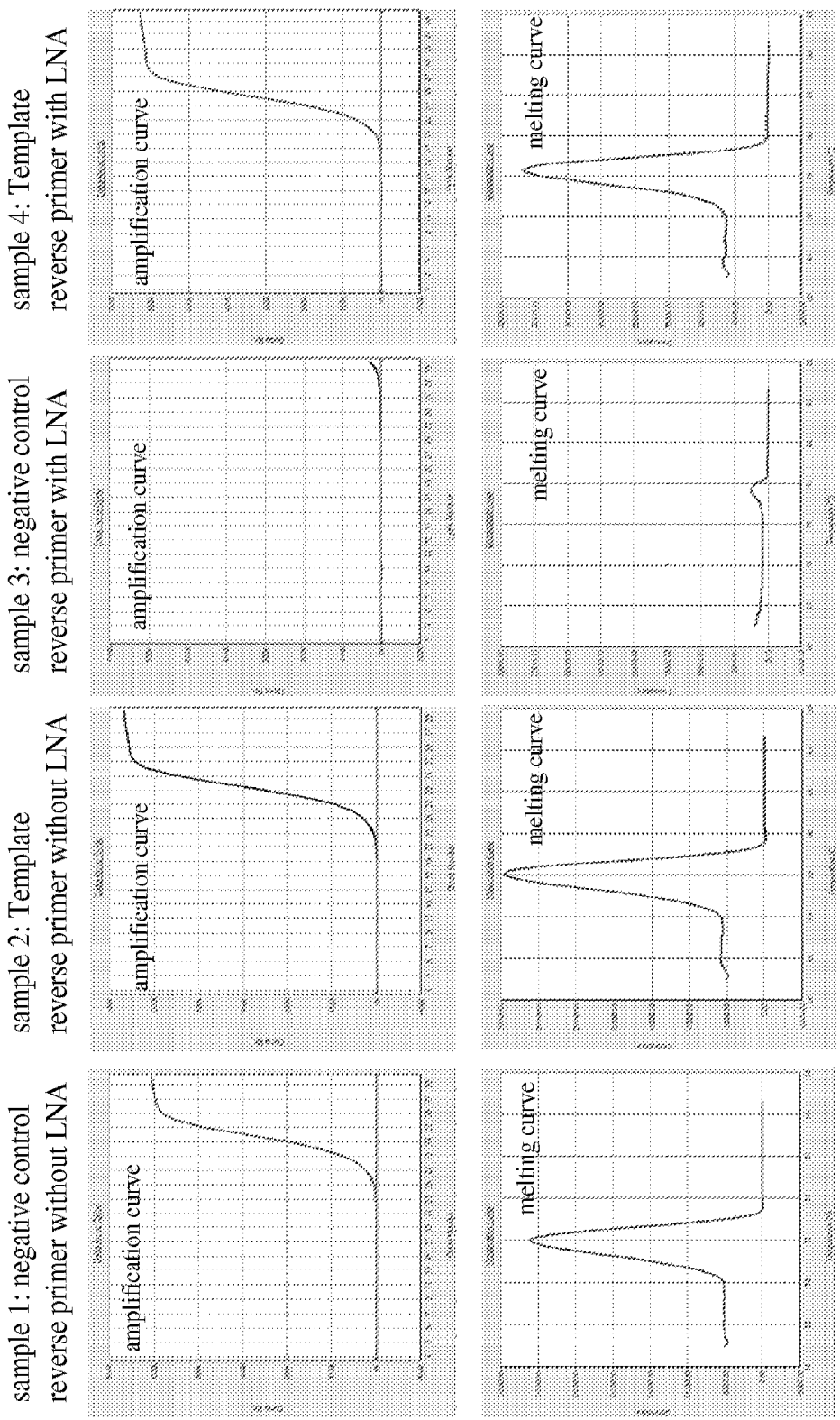
FIG. 3 shows the amplification curves and the first derivative of the melting curves of Example 2

Amplification of the correct product was measured according to the recommendations from the manufacturer of the thermocycler (Applied Biosystems, Foster City, Calif., US). Briefly, the PCR reaction was incubated at 60° C. for 1 minute and fluorescence was measured during a slow increase of the temperature to 95° C. The first derivative of the melting curves is shown in FIG. 3:

The results show (FIG. 3) that the reverse primer without LNA (r7a.2) gives a positive signal in the negative control whereas the reverse primer with LNA (r7a.7) does not. Thus the LNA base in r7a.7 is necessary in order to avoid an unspecific PCR product developed in the negative control reaction. Both primers amplify the positive control template.

As can be seen from table 2, it was found that the inclusion of one LNA in the miR-specific sequence of the reverse primer reduced background signal in PCR.

TABLE 2

Effect of LNA in primer pairs for miR specific qPCR

| hsa-miR | Forward primer 5' → 3 | Reverse primer 5' → 3 | $C_T$ Negative control | $C_T$ Template |
|---|---|---|---|---|
| let-7a | tGaGgtagtaggttg (SEQ ID NO 7) | cggtgacacggaggtactagttttttttttttttttaactata (SEQ ID NO 8) | 28 | 25 |
|  |  | cggtgacacggaggtactagttttttttttttttttaamCtata (SEQ ID NO 9) | nd | 24 |
| miR-16 | tAcmCagcacgtaaa (SEQ ID NO 10) | cacggaggtactagttttttttttttttttcgccaat (SEQ ID NO 11) | 27 | 24 |
|  |  | cacggaggtactagttttttttttttttttmCgccaat (SEQ ID NO 12) | nd | 26 |

TABLE 2-continued

Effect of LNA in primer pairs for miR specific qPCR

| hsa-miR | Forward primer 5' → 3 | Reverse primer 5' → 3 | $C_T$ Negative control | $C_T$ Template |
|---|---|---|---|---|
| miR-21 | tAcmCttatcagactgatg (SEQ ID NO 13) | gcggtgacacggaggtactagttttttttttttttcaac (SEQ ID NO 14) | 32 | 25 |
|  |  | gcggtgacacggaggtactagttttttttttttttmCaac (SEQ ID NO 15) | 38 | 24 |
| miR-23a | atmCamCattgccag (SEQ ID NO 16) | tgacacggaggtactagttttttttttttttggaaatc (SEQ ID NO 17) | 34 | 25 |
|  |  | tgacacggaggtactagttttttttttttttGgaaatc (SEQ ID NO 18) | 39 | 26 |
| miR-150 | tmCtmCccaacccttg (SEQ ID NO 19) | tgacacggaggtactagttttttttttttttmCactggta (SEQ ID NO 20) | 28 | 23 |
|  |  | tgacacggaggtactagttttttttttttttcactggta (SEQ ID NO 21) | 38 | 25 |
| miR-208a | ataaGamCgAgcaaaaag (SEQ ID NO 22) | mCggtgacacggaggtactagttttttttttttttacaagc (SEQ ID NO 23) | 35 | 25 |
|  |  | cggtgacacggaggtactagttttttttttttttAcaagc (SEQ ID NO 24) | nd | 26 |
|  |  | cggtgacacggaggtactagttttttttttttttTacaagc (SEQ ID NO 25) | nd | 26 |

Lower case designates natural occurring nucleotides, upper case designates LNA,: mC denotes LNA methyl cytosine, CT designates cycle threshold, nd, not detectable.

Example 3

Manual Primer Design and Validation of Primers for miRs

Primers were manually designed following the design-rules presented in the "primer design"-part of the DEFINITIONS section.

Primer Validation:

By using the primer design rules it is possible to achieve PCR primers that have >70% success rate in real-time PCR experiments according to the following validation criteria:
Prepare Rtmix for four reverse transcription (RT) samples:
1. Water
2. 100 ng total human RNA mix* (as default we use a mix of 25 ng of each heart, brain, liver and lung total RNA from Ambion).
   *RNA mix: 1 µl 1 µg/µl heart RNA, 1 µl 1 µg/µl brain RNA, 1 µl 1 µg/µl liver RNA, 1 µl 1 µg/µl lung RNA, 36 µl TE. Store in 1 µl aliquots at −80° C.
3. 100 ng total human RNA mix without PolyA tailing.
4. $10^7$ copies of the synthetic miR in 10 ng phage MS2 RNA in TE (synthetic miRs were obtained from Integrated DNA technologies Inc., Coralville, Iowa, US.). The miR can be added as a pool comprising up to at least 20 miRs.

| RTmix | Total |
|---|---|
| 10x PAP buffer | 4.4 µl |
| 1 mM ATP | 4.4 µl |
| 1 µM L6TA RTprimer | 4.4 µl |
| 4x 1 mM dNTP | 4.4 µl |
| Transcriptor 1:10 | 2.2 µl |
| Water | 11 µl |

PAP buffer = Poly(A) polymerase buffer (New England Biolabs).
L6TA = 5'-tgcggtgacacggaggtactagttttttttttttttVN (SEQ ID NO 129).
Transcriptor = Reverse Transcriptase. (Roche Diagnostics A/S, Hvidovre, Denmark, cat# 03 531 295 001).

Reverse Transcription Reactions:

| sample | 0.1 µg/µl RNAmix* | 1 µl | water | 0.5 U/µl PAP$^a$ (NEB) | RTmix |
|---|---|---|---|---|---|
| #1 |  |  | 1 µl | 2 µl | 7 µl |
| #2 | 1 µl |  |  | 2 µl | 7 µl |
| #3 | 1 µl |  | 2 µl |  | 7 µl |
| #4 |  | 1e7miR |  | 2 µl | 7 µl |

Incubate 42° C., 1 h > 95° C., 5'
Add 90 µl TE to each sample and store at −20° C.
$^a$Remember to dilute the poly(A) polymerase (PAP) 1:10 before use!

miR-specific qPCR:

Run PCR with the forward and reverse primers on 1 µl of each reverse transcription (RT) reaction:

| Sample | 1 µl RT reaction | 5 µM forward primer | 5 µM reverse primer | 2xfaststart | Water |
|---|---|---|---|---|---|
| #1 | #1 | 0.5 µl | 0.5 µl | 10 µl | 8 µl |
| #2 | #2 | 0.5 µl | 0.5 µl | 10 µl | 8 µl |
| #3 | #3 | 0.5 µl | 0.5 µl | 10 µl | 8 µl |
| #4 | #4 | 0.5 µl | 0.5 µl | 10 µl | 8 µl |

Real-Time PCR on the ABI 7500:
95° C., 10 min
95° C., 15 sec; 60° C., 60 sec; 40 cycles
Run melting curve analysis Acceptance Criteria:
Sample 1: Cycle threshold ($C_t$) above 40 compared to exponential area for #2 and 4.
  Melting peak derivative below 5000.
Sample 2: $C_t$ below 35
  One peak on bell shaped melting curve, unless otherwise justified the peak should be between 69° C. and 80° C. Peak at same temperature (+/−0.5° C.) as in sample 4.
  In the exponential area the crossing point at 10 times delta Rn minus the crossing point at delta Rn should be between 3.2 and 4.4: $3.2 < (C10T - CT) < 4.4$ Sample 3: $C_t$ above 40 compared to exponential area for #2 and 4.
Melting peak derivative below 5000.
Sample 4: One peak on bell shaped melting curve, unless otherwise justified the peak should be between 69° C. and 80° C. Peak at same temperature (+/−0.5° C.) as in sample 2.

TABLE 3

Design and validation of 17 primer pairs

| miR | Forward primer 5' → 3 | SEQ ID NO | Reverse primer 5' → 3 | SEQ ID NO | Assay valid? |
|---|---|---|---|---|---|
| hsa-miR-124 | taaGgcacgcggtga | 26 | tgacacggaggtactagtttttttttttttttTggcat | 43 | Yes |
| hsa-miR-9 | ctgtmCtttGgttatctag | 27 | tgacacggaggtactagtttttttttttttttmCatacag | 44 | Yes |
| hsa-miR-181a | aamCattmCaacgctgt | 28 | tgacacggaggtactagtttttttttttttttamCtcac | 45 | Yes |
| hsa-miR-128 | tmCamCagtgaaccggt | 29 | tgacacggaggtactagtttttttttttttttAaagaga | 46 | Yes |
| hsa-miR-488 | ttGaaaGgctatttc | 30 | tgacacggaggtactagtttttttttttttttGacca | 47 | No |
| hsa-miR-328 | ctggccctctctgcc | 31 | tgacacggaggtactagtttttttttttttttAcggaa | 48 | Yes |
| hsa-miR-324 | cgcatcccctagggcat | 32 | tgacacggaggtactagtttttttttttttttAcacca | 49 | Yes |
| hsa-miR-331 | cTaGgtatggtccca | 33 | tgacacggaggtactagtttttttttttttttGgatc | 50 | No |
| hsa-miR-34a | tGgcAgtgtcttagc | 34 | tgacacggaggtactagtttttttttttttttamCaacca | 51 | Yes |
| hsa-miR-130a | caGtGcaatgttaaaag | 35 | tgacacggaggtactagtttttttttttttttAtgc | 52 | No |
| hsa-miR-1 | tGgAatgtaaagaagt | 36 | tgacacggaggtactagtttttttttttttttAtacata | 53 | No |
| hsa-miR-23b | atmCamCattgccag | 37 | tgacacggaggtactagttttttttttttttttggTaatc | 54 | Yes |
| hsa-miR-133a | tTtGgtccccttcaa | 38 | tgacacggaggtactagtttttttttttttttGagctg | 55 | Yes |
| hsa-miR-133b | tTtGgtccccttcaa | 39 | tgacacggaggtactagtttttttttttttttAgctg | 56 | Yes |
| hsa-miR-93 | cAaaGtgctgttcgtg | 40 | tgacacggaggtactagtttttttttttttttmCtacctg | 57 | No |
| hsa-miR-181b | aamCattmCattgctgtc | 41 | tgacacggaggtactagtttttttttttttttAccca | 58 | Yes |
| hsa-miR-24 | tGgctmCagttcagca | 42 | tgacacggaggtactagtttttttttttttttmCtgttc | 59 | Yes |
| | | | | | Total: 12/17 = 71% |

Lower case designates natural occuring nucleotides, upper case designates LNA, mC denotes LNA methyl cytosine.

Result (see tab 3): Seventeen primers pairs were designed according to the design rules. Twelve of the 17 assays were successfully validated according to the validation protocol corresponding to a success rate of 71%.

TABLE 4

Design and validation of 15 primer pairs. The theoretical $T_m$ of the reverse primer was optimised to 59° C.:

| miR | Forward primer 5' → 3 | SEQ ID NO | Reverse primer 5' → 3 | SEQ ID NO | Assay valid? |
|---|---|---|---|---|---|
| hsa-miR-146b | ctgtGagaactgaattcca | 60 | gtactagtttttttttttttttAgcct | 75 | Yes |
| hsa-miR-146b-3p | tgccctgtggactca | 61 | gtactagtttttttttttttttmCcagaac | 76 | Yes |
| hsa-miR-429 | ctgtaatamCtGtctggta | 62 | gtactagtttttttttttttttAcggtt | 77 | Yes |
| hsa-miR-193a-3p | aactggcctacaaagtcc | 63 | gtactagtttttttttttttttamCtgg | 78 | Yes |
| hsa-miR-193a | gtctttgcgggcga | 64 | ggtactagtttttttttttttttmCatct | 79 | Yes |
| hsa-miR-193b | aamCtggccctcaaag | 65 | gaggtactagttttttttttttttttmCatct | 80 | Yes |
| hsa-miR-149 | tmCtggcTccgtgtcttca | 66 | tagttttttttttttttttgggAgtg | 81 | Yes |
| hsa-miR-452 | aamCtGtttgcagaggaa | 67 | gtactagtttttttttttttttmCagtt | 82 | Yes |
| hsa-miR-452* | ctmCatmCtgcaaagaagta | 68 | gtactagtttttttttttttttmCactt | 83 | No |
| hsa-miR-30b | tGtaaamCatcctacactc | 69 | gtactagttttttttttttttttaGctga | 84 | No |
| hsa-miR-34b | ctgcaatcactaactccact | 70 | gaggtactagtttttttttttttttttAtgg | 85 | Yes |
| hsa-miR-34c | aggcaGtgtagttagctg | 71 | tactagtttttttttttttttttGcaatca | 86 | Yes |
| hsa-miR-134 | tgtgactggttgaccaga | 72 | gtactagtttttttttttttttttTcccct | 87 | Yes |
| hsa-miR-671 | ctgaGgaagccctgga | 73 | gtactagtttttttttttttttmCtcca | 88 | No |
| hsa-miR-769-3p | ctgggatctccggggtct | 74 | aggtactagttttttttttttttttAacca | 89 | Yes |
|  |  |  |  |  | Total: 12/15 = 80% |

Lower case designates natural occuring nucleotides, upper case designates LNA, mC denotes LNA methyl cytosine.

Result (see tab 4): 15 primers pairs were designed according to the design rules. 12 of the 15 assays were successfully validated according to the validation protocol corresponding to a success rate of 80%.

Example 4

Discrimination Between Targets with a Single Nucleotide Difference

There are three miRs that only differ by one nucleotide from the sequence of hsa-let-7a (table below).

TABLE 5

Nucleotide sequence of let-7 family miRNAs

| miR | Sequence[a] |
|---|---|
| hsa-let-7a | 5'-ugagguaguagguuguauaguu-3' (SEQ ID NO 90) |
| hsa-let-7f | 5'-ugagguaguagauuguauaguu-3' (SEQ ID NO 91) |

TABLE 5-continued

Nucleotide sequence of let-7 family miRNAs

| miR | Sequence[a] |
|---|---|
| hsa-let-7c | 5'-ugagguaguagguuguaugguu-3' (SEQ ID NO 92) |
| hsa-let-7e | 5'-ugagguaggagguuguauaguu-3' (SEQ ID NO 93) |

[a] The difference between the four closely related members of the let-7 family is indicated by bold letters.

To test if the qPCR primers for hsa-let-7a detect the miRs with a single nucleotide difference the following miR-specific qPCR experiment was performed:

Mixed on Ice:

RT Mix:

1 µl 10×PAP buffer (Epicentre Biotechnologies, Madison, Wis., US.)

1 µl 1 mM ATP

1 µl 10 µM RT-primer (L2TA: 5'-ggtactagttttttttttttttvn (SEQ ID NO 5), v designates c, g and a, n designates c, g, a and t))

1 µl mix of 1 mM dATP, 1 mM dCTP, 1 mM dGTP, 1 mN dTTP 0.5 µl 2 units/µl Transcriptor (Roche Diagnostics A/S, Hvidovre, Denmark, cat#03 531 295 001).

0.2 µl (5 U/µl) Poly(A) polymerase (Epicentre)

4.5 µl water

The following samples were prepared and incubated at 42° C., 1 hour followed by 95° C., 5 minutes:

| Synthetic template | RT mix |
|---|---|
| 1 µl 10 ng/µl phage MS2 RNA in TE | 9 µl |
| 1 µl $10^8$ copies of hsa-let-7a[1] | 9 µl |
| 1 µl $10^8$ copies of hsa-let-7f[1] | 9 µl |
| 1 µl $10^8$ copies of hsa-let-7c[1] | 9 µl |
| 1 µl $10^8$ copies of hsa-let-7e[1] | 9 µl |

[1]The synthetic templates were prepared in 10 ng/µl phage MS2 RNA in TE. The synthetic templates are obtained from Integrated DNA technologies Inc., Coralville, IA, US.

For qPCR 1 µl of the polyA tailing/RT reaction was used for each PCR reaction with the hsa-let-7a forward primer 5'-tGaGgtagtaggttg (SEQ ID NO 7) and reverse primer 5'-cg-paggtactagttttttttttttttAactat (SEQ ID NO 94)

Real-time PCR was done on a ABI 7500 thermocycler by monitoring SYBR® green fluorescence as a function of PCR cycle number. The PCR reaction mixture contained:

10 µl 2×PCR mastermix (Roche cat#04 673 484 001)

1 µl or less of the RT reaction

1 µl TE with 2.5 µM miR-specific forward primer and 2.5 µM miR-specific reverse primer water to 20 µl.

The mixture was incubated at 95° C. for 10 min followed 40 cycles of 95'C for 5 sec; 60° C. for 60 sec with measurement of the fluorescence.

Amplification of the correct product was measured by comparing the melting curve profile of the PCR product to the melting curve profile of a PCR product obtained by amplification of a synthetic template.

The result of the real-time PCR experiment was analysed according to standard methods (Bustin, S A (ed.) "A-Z of Quantitative PCR." International University Line (La Jolla, Calif., USA), 2004).

Figure 4:
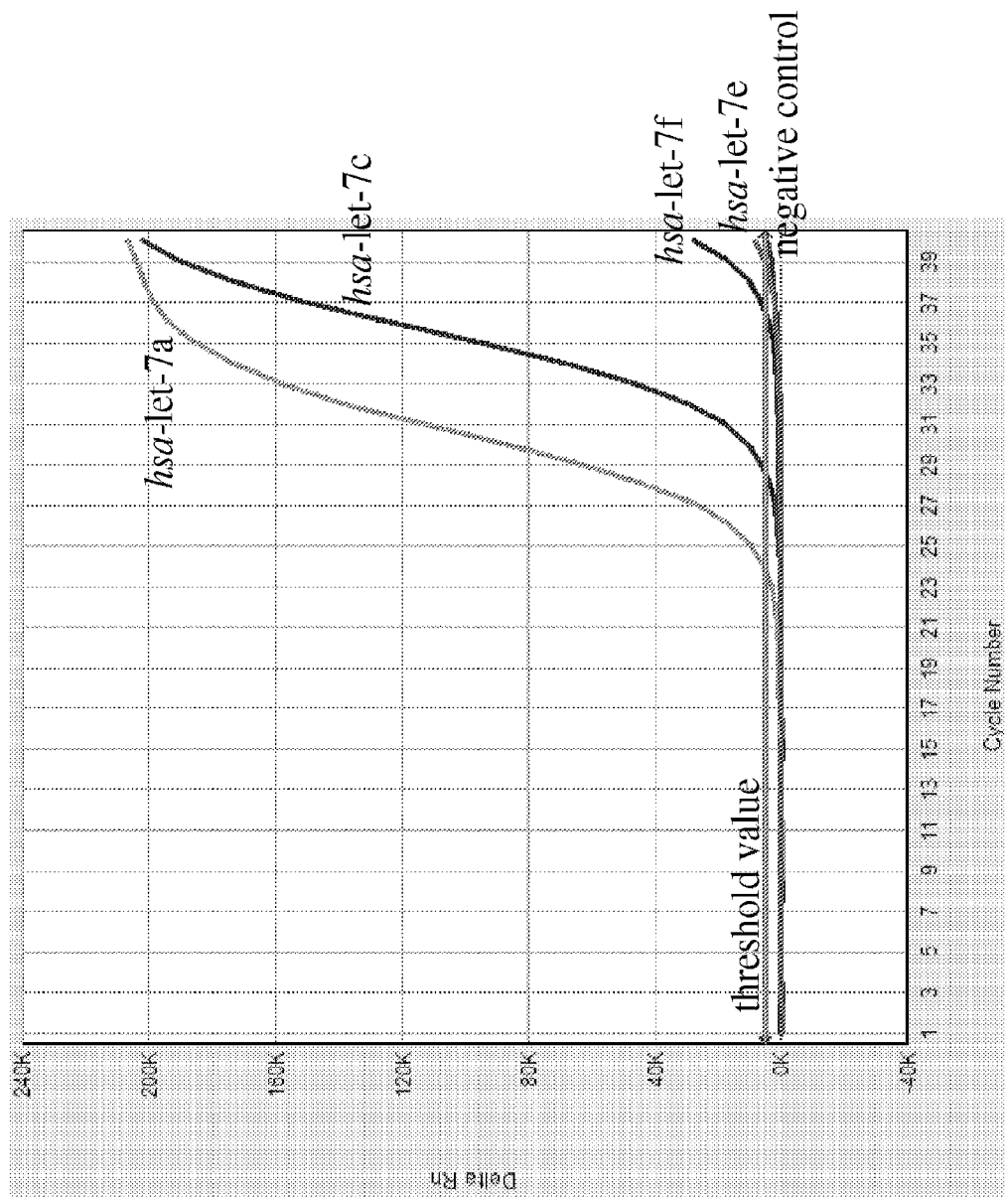
FIG. 4 shows amplification plots of Example 4 wherein discrimination between hsa-let-7a and the variants hsa-let-7f, hsa-let-7c and hsa-let-7e are demonstrated. The amplification-signal from negative controls are also indicated.

The result is shown in table 6 and as amplification plots in FIG. 4.

TABLE 6

| Template | $C_\tau$ | % of signal on hsa-let-7a template[2] |
|---|---|---|
| 10 ng/µl phage MS2 RNA | nd[1] | 0 |
| hsa-let-7a | 25 | 100 |
| hsa-let-7f | 38 | 0.01 |

TABLE 6-continued

| Template | $C_\tau$ | % of signal on hsa-let-7a template[2] |
|---|---|---|
| hsa-let-7c | 30 | 4 |
| hsa-let-7e | nd | 0 |

[1]nd, not detected

[2]The percent signal was calculated as $100/2^{(C_\tau (template) - C_\tau (hsa-let-7a))}$ assuming an amplification efficiency of 100.

Example 5

Quantification of miRs in Human Brain Total RNA

In this example the copy number of miRs hsa-let-7a, hsa-miR-21, hsa-miR-27b and hsa-miR-195 in total human brain RNA (Ambion) was determined.

Mixed on Ice:

RT Mix:

1 µl 10×PAP buffer (New England Biolabs)

1 µl 1 mM ATP

1 µl 10 µM RT-primer (L2TA: 5'-ggtactagtttttttttttttttvn (SEQ ID NO 5), v designates cytosine, guanine and adenine residues, n designates cytosine, guanine, adenine and thymine residues)).

1 µl mix of 1 mM dATP, 1 mM dCTP, 1 mM dGTP, 1 mM dTTP 0.5 µl 2 units/µl Transcriptor (Roche cat#03 531 295 001, Roche Diagnostics A/S, Hvidovre, Denmark).

0.5 µl (5 U/µl) Poly(A) polymerase (New England Biolabs Inc., Ipswich, Mass., US)

3 µl water

The following samples were prepared and incubated at 42° C., 1 hour followed by 95° C., 5 minutes:

| Synthetic template/water | Phage MS2 RNA in TE (10 ng/µl) | Human brain RNA (10 ng/µl) | RT mix |
|---|---|---|---|
| 1 µl water | 1 µl | | 8 µl |
| 1 µl~$10^2$ copies | 1 µl | | 8 µl |
| 1 µl~$10^3$ copies | 1 µl | | 8 µl |
| 1 µl~$10^4$ copies | 1 µl | | 8 µl |
| 1 µl~$10^5$ copies | 1 µl | | 8 µl |
| 1 µl~$10^6$ copies | 1 µl | | 8 µl |
| 1 µl~$10^7$ copies | 1 µl | | 8 µl |
| 1 µl~$10^8$ copies | 1 µl | | 8 µl |
| 1 µl~$10^9$ copies | 1 µl | | 8 µl |
| 1 µl water | | 1 µl | 8 µl |

Synthetic template: Equal amounts (number of copies) of synthetic hsa-let-7a, hsa-miR-21, hsa-miR-27b and hsa-miR-195 in 10 ng/µl phage MS2 RNA in TE (obtained from Integrated DNA technologies Inc).

TE: 10 mM Tris/HCl (pH 8.0), 1 mM EDTA.

For qPCR 1 µl of the polyA tailing/RT reaction was used for each PCR reaction with the gene-specific primers:

TABLE 7

| miR | Forward primer 5' → 3 | Reverse primer 5' → 3 |
|---|---|---|
| hsa-let-7a | tGaGgtagtaggttg (SEQ ID NO 7) | tgacacggaggtactagttttttttttttttAactat (SEQ ID NO 94) |
| hsa-miR-21 | tAgmCttatcagactgatg (SEQ ID NO 13) | gcggtgacacggaggtactagttttttttttttttttmCaac (SEQ ID NO 15) |
| hsa-miR-27b | ttmCamCagtggctaag (SEQ ID NO 95) | tgacacggaggtactagttttttttttttttttGcaga (SEQ ID NO 96) |
| hsa-miR-195 | ctgtaGcaGcacagaa (SEQ ID NO 97) | tgacacggaggtactagttttttttttttttttGccaat (SEQ ID NO 98) |

Real-time PCR was done on a ABI 7500® thermocycler by monitoring SYBR® green fluorescence as a function of PCR cycle number. The PCR reaction mixture contained:
- 10 µl 2×PCR mastermix (Roche cat#04 673 484 001)
- 1 µl or less of the RT reaction
- 1 µl TE with 2.5 µM miR-specific forward primer and 2.5 µM miR-specific reverse primer
- water to 20 µl.

The mixture was incubated at 95° C. for 10 min allowed 40 cycles of 95° C. for 5 sec; 60° C. for 60 sec with measurement of the fluorescence.

Amplification of the correct product was measured by comparing the melting curve profile of the PCR product to the melting curve profile of a PCR product obtained by amplification of a synthetic template.

For each miR, the result of the real-time PCR experiment was analysed according to standard methods (Bustin, S A (ed.) "A-Z of Quantitative PCR." International University Line (La Jolla, Calif., USA), 2004) and the Ct values from the samples without human brain RNA was used to construct standard curves.

The $C_t$ of the sample with human brain RNA was compared to the standard curve to determine the number of miRs in the sample (Bustin, S A (ed.) "A-Z of Quantitative PCR." International University Line (La Jolla, Calif., USA), 2004).

Results:

TABLE 8

| miR | Copies per 10 pg brain RNA |
|---|---|
| hsa-let-7a | 16000 |
| hsa-miR-21 | 400 |
| hsa-miR-27b | 400 |
| hsa-miR-195 | 1000 |

Example 6

Design of premiR qPCR Assays

This example shows that the hsa-miR-10a assay does not detect the corresponding premiR, hsa-premiR-10a. Similarly, it is possible to use the primer design to make an assay that detects hsa-premiR-10a but not hsa-miR-10a.

Mixed on Ice:
RT Mix:
- 1 µl 10×PAP buffer (New England Biolabs)
- 1 µl 1 mM ATP
- 1 µl 10 µM RT-primer (L2TA: 5'-ggtactagttttttttttttttttvn (SEQ ID NO 5), v designates cytosine, guanine and adenine residues, n designates cytosine, guanine, adenine and thymine residues)).
- 1 µl mix of 1 mM dATP, 1 mM dCTP, 1 mM dGTP, 1 mM dTTP
- 0.5 µl 2 units/µl Transcriptor (Roche cat#03 531 295 001).
- 0.5 µl (5 U/µl) Poly(A) polymerase (New England Biolabs)
- 3 µl water The following samples were prepared and incubated at 42° C., 1 hour followed by 95° C., 5 minutes:

| RNA sample | RT mix |
|---|---|
| 1 µl~water | 9 µl |
| 1 µl~10⁶ copies hsa-miR-10a | 9 µl |
| 1 µl~10⁶ copies hsa-premiR-10a | 9 µl |

For qPCR 1 µl of the polyA tailing/RT reaction was used for each PCR reaction with the specific primers in Table 9.

TABLE 9

| Target | Forward primer (5' → 3) | Reverse primer (5' → 3) |
|---|---|---|
| hsa-miR-10a | tAccctGtagatccgaa (SEQ ID NO 99) | tgacacggaggtactagttttttttttttttttCacaaat (SEQ ID NO 100) |
| hsa-premiR-10a | tgtGtaaggaattttgtggt (SEQ ID NO 101) | gaggtactagttttttttttttttttAttc (SEQ ID NO 102) |

Real-time PCR was done on a ABI 7500 thermocycler by monitoring SYBR® green fluorescence as a function of PCR cycle number. The PCR reaction mixture contained:
- 10 µl 2×PCR mastermix (Roche cat#04 673 484 001)
- 1 µl or less of the RT reaction
- 1 µl TE with 2.5 µM miR-specific forward primer and 2.5 µM miR-specific reverse primer
- water to 20 µl.

The mixture was incubated at 95° C. for 10 min followed 40 cycles of 95'C for 5 sec; 60'C for 60 sec with measurement of the fluorescence.

For each miR, the result of the real-time PCR experiment was analysed according to standard methods (Bustin, S A (ed.) "A-Z of Quantitative PCR." international University Line, 2004).

| RNA sample | RT mix |
|---|---|
| 1 µl water | 9 µl |
| 1 µl~100 ng/µl RNA mix[a] | 9 µl |
| 1 µl~$10^6$ copies hsa-miR-10a | 9 µl |
| 1 µl~$10^6$ copies hsa-premiR-10a | 9 µl |

[a]Mixture of 1 µl of 1 µg/µl heart RNA, 1 µl of 1 µg/µl brain RNA, 1 µl of 1 µg/µl liver RNA, 1 µl of 1 µg/µl lung RNA, 1 µl of 1 µg/µl kidney RNA, 1 µl of 1 µg/µl lymph RNA, 1 µl of 1 µg/µl jejunum RNA, 1 µl of 1 µg/µl colon RNA, 1 µl of 1 µg/µl breast RNA and 1 µl of 1 µg/µl leukemia RNA in TE.
TE buffer: 10 mM Tris/HCl (pH 8.0), 1 mM EDTA.

For qPCR 1 µl of the polyA tailing/RT reaction was used for each PCR reaction with the specific primers in Table 11.

TABLE 11

| Target | Forward primer 5' → 3 | reverse primer 5' → 3 |
|---|---|---|
| hsa-miR-10a | tAccctGtagatccgaa (SEQ ID NO 99) | tgacacggaggtactagttttttttttttttmCacaaat (SEQ ID NO 100) |
| hsa-premiR-10a | tgtGtaaggaatttgtggt (SEQ ID NO 101) | gaggtactagtttttttttttttttAttc (SEQ ID NO 102) |

TABLE 10

| RNA | hsa-miR10a assay | hsa-premiR10a assay |
|---|---|---|
| negative control | below detection | below detection |
| hsa-miR10a | $C_\tau$ = 29.53 | below detection |
| hsa-premiR10a | below detection | $C_\tau$ = 30.82 |

The result shows that both the hsa-miR-10a and the hsa-premiR-10a assays detect the correct target and that there is no cross reaction to premiR-10a or miR-10a, respectively.

Example 7

Detection of pre-miR by qPCR

In this example hsa-miR-10a and the corresponding pre-miR, hsa-pre-miR-10a were detected in total human RNA.
Mixed on Ice:
RT Mix:
- 1 µl 10×PAP buffer (New England Biolabs Inc., Ipswich, Mass., US)
- 1 µl 1 mM ATP
- 1 µl 10 µM RT-primer (L2TA: 5'-ggtactagttttttttttttttvn (SEQ ID NO 5), v designates cytosine, guanine and adenine residues, n designates cytosine, guanine, adenine and thymine residues)).
- 1 µl mix of 1 mM (ATP, 1 mM dCTP, 1 mM dGTP, 1 mM dTTP
- 0.5 µl 2 units/µl Transcriptor (Roche cat#03 531 295 001).
- 0.5 µl (5 U/µl) Poly(A) polymerase (New England Biolabs)
- 3 µl water The following samples were prepared and incubated at 42° C., 1 hour followed by 95° C., 5 minutes:

Real-time PCR was done on a ABI 7500 thermocycler by monitoring SYBR® green fluorescence as a function of PCR cycle number. The PCR reaction mixture contained:
- 10 µl 2×PCR mastermix (Roche cat#04 673 484 001)
- 1 µl or less of the RT reaction
- 1 µl TE with 2.5 µM miR-specific forward primer and 2.5 µM miR-specific reverse primer
- water to 20 µl.

The mixture was incubated at 95° C. for 10 min followed 40 cycles of 95° C. for 5 sec; 60'C for 60 sec with measurement of the fluorescence.

For each miR, the result of the real-time PCR experiment was analysed according to standard methods (Bustin, S A (ed.) "A-Z of Quantitative PCR." International University Line, 2004). The result is shown in tab 12.

TABLE 12

| RNA | hsa-miR10a assay | hsa-premiR10a assay |
|---|---|---|
| negative control | below detection | below detection |
| total RNA | $C_\tau$ = 26.22 | $C_\tau$ = 37.25 |
| hsa-miR10a | $C_\tau$ = 28.83 | not testet |
| hsa-premiR10a | not testet | $C_\tau$ = 32.59 |

The result shows that the total RNA sample contains more than $10^6$ copies of hsa-miR-10a because the $C_T$ is below the $C_T$ of the sample with $10^6$ copies of hsa-miR-10a whereas the total RNA sample contains less than $10^6$ copies of hsa-premiR-10a because the $C_T$ is below the $C_T$ of the sample with $10^6$ copies of hsa-premiR-10a.

Example 8

Specific Detection of Pre-miRNAs

Aim of the experiment: To determine if the universal reverse transcriptase quantitative PCR methodology (UniRT qPCR) described in this application could be used to detect pre-miR specifically without co-detection of the corresponding mature miR.

Materials: Synthetic miR 203 RNA (5'-gugaaauguuuag-gaccacuag) (SEQ ID NO 103) and pre-miR 203 RNA (5'-agugguucuuaacaguucaacaguucugu-agcgcaauugugaaaugu-uuaggaccacuag) (SEQ ID NO 104) were selected as test subjects. The synthetic RNAs were synthesized by Integrated DNA technologies Inc., Coralville, Iowa, US. The RNAs were diluted to $1*10^6$ molecules/μL in TEMS2 (TE buffer (10 mM Tris HCl pH 8, and 0.1 mM EDTA mixed with 10 ng/μL. MS2 viral RNA (Roche Applied Science Inc). Primers used were miR-203.Rev (5'-tgacacggaggtactagtttttttttttttttCtag) (SEQ ID NO 105), miR-203.Fwd (5'-gtGaaatGtttaggacca) (SEQ ID NO 106) and pre-miR-203. Fwd (5'-cagttcaacagt-tctgtagc) (SEQ ID NO 107). The pre-miR-203 Fwd primer was designed in the loop structure of the pre-miR-203 molecule. Mature miR-203 template and pre-miR-203 were subject to reverse transcription using Universal cDNA synthesis kit (Exiqon AS, Cat. no #203300).

| Mix: | |
| --- | --- |
| Synthetic RNA | 1 * 10^6 molecules |
| 5 x UniRT reaction buffer | 2 μL |
| 10x Enzyme mixture | 1 μL |
| Water | up to 10 μL |

Incubate at 42° C. for 60 minutes and heat denature at 85° C. for 5 minutes. Dilute 10× in water.

qPCR with SYBR Green Master Mix, UniRT (Exiqon AS, Cat. No. 203400)

| Mix | |
| --- | --- |
| Primer mix (3 uM each) | 1 μL |
| SYBR green master mix | 5 μL |
| cDNA template | 1 μL |
| Water | 3 μL |

Two primer mixes were used; 1) miR-203 ((miR-203.Fwd and miR-203.Rev primer) and 2) pre-miR-203 (pre-miR-203.Fwd and miR-203.Rev primer). Templates used were mir-203 and pre-mir-203. Non template control (NTC) qPCR was also run for each PCR assay. All qPCR were done in duplicates.

q-RT-PCR reactions were performed in a 384 well plate in a LightCycler 480 (Roche Diagnostics) instrument using the following PCR protocol
1. 95° C. for 10 minutes
2. 95° C. for 10 seconds
3. 60° C. for 1 minute Signal detection with SYBR green (HRM dye) setup. Steps 2-3 repeated for 45 times followed by melting curve analysis.

Results and Discussion

Standard miR-203 primers detect the miR-203 template well with a Cp value of 28.86. Also the miR-203 assay, partially detects the pre-miR-203 (Cp of 30.125) since the miR is located on the 3' end of the pre-mir-203. Pre-miR-203 assay design detects the pre-miR with the Cp values of 25.7 however the mature miR-203 is not detected with the pre-miR-203 specific assay (Cp=40). This data clearly shows that pre-mir specific assays can be designed to specifically target the pre-miR molecules.

TABLE 13

Detection of pre-miR-203 and miR-203 using miR specific primer and pre-mir specific primers.

| Template | Assay | Mean Cp | Percent detection |
| --- | --- | --- | --- |
| NTC | miR-203 | | |
| miR-203 | miR-203 | 28.86 | 100.0 |
| pre-miR-203 | miR-203 | 30.125 | 41.6 |
| NTC | Pre-miR-203 | | |
| miR-203 | Pre-miR-203 | 40 | 0.0 |
| pre-miR-203 | Pre-miR-203 | 25.675 | 100 |

Mean Cp represents a mean value of a duplicate qPCR reaction.
Percent detection is estimated as a = 100/POWER(2; (Cp_test − Cp_ref)) where the Cp_ref is the corresponding template and primer set Cp value.

Example 9

Micro-RNAs Differentially Expressed in Heart and Liver Tissues

Aim of the experiment is to determine if well expressed miRNAs that are differently expressed between heart and liver tissue can be discriminated using a qPCR array based on the SYBR green universal reverse transcriptase quantitative PCR (UniRT qPCR) method of the present invention.

Materials and Methods

Total RNA from liver and whole-heart was obtained from Ambion Inc., and diluted in nuclease free water to a concentration of 10 ng/μL and stored at −80° C. We selected a few mRNA that are known to be differentially expressed in heart and liver tissue samples from the literature (see for example: Liang, Y., et al. (2007) EMC Genomics. 8: pp 166 and Landgraf P., et al. (2007) Nature Biotechnol. (9): pp 996-7). The miR selected were hsa-miR-1, hsa-miR-126 and hsa-miR-133b (heart) and hsa-miR-192, hsa-miR-122*, hsa-miR-194 and hsa-miR-122 (liver).

TABLE 14

Primer sequences for the seven mIR assays. Capital letters represent LNA nucleotides.

| Assay | Reverse primer (5 → 3) | SEQ ID NO | Forward primer (5 → 3) | SEQ ID NO |
| --- | --- | --- | --- | --- |
| hsa-miR-122 | tgacacggaggtactagtttttttttttttttCaaacac | 108 | tGgaGtgtgacaatg | 115 |
| hsa-miR-194 | gtactagtttttttttttttttCcaca | 109 | tGtaaCagcaactcca | 116 |
| hsa-miR-122* | gaggtactagtttttttttttttttAtttag | 110 | aAcgccAtTatcacact | 117 |
| hsa-miR-192 | gtactagtttttttttttttttGgct | 111 | tgactGacCtatgaattgac | 118 |

TABLE 14-continued

Primer sequences for the seven mIR assays. Capital letters represent LNA nucleotides.

| Assay | Reverse primer (5 → 3) | SEQ ID NO | Forward primer (5 → 3) | SEQ ID NO |
|---|---|---|---|---|
| hsa-miR-126 | gtactagttttttttttttttTcgcat | 112 | ctgtCgtaccgtgagta | 119 |
| hsa-miR-133b | tgacacggaggtactagtttttttttttttttAgctg | 113 | tTtGgtccccttcaa | 120 |
| hsa-miR-1 | tgacacggaggtactagtttttttttttttttAtacata | 114 | ctgtGgAatgtaaagaagt | 121 |

Capital letters represent LNA nucleotides.

RT reactions were performed in triplicate for each tissue and non enzyme control (NEC)) with Universal cDNA synthesis kit (Exiqon AS, Cat. no #203300)

| total RNA | 20 ng |
| 5 x UniRT reaction buffer | 4 µL |
| Enzyme mixture | 2 µL |
| Water | up to 20 µL |

Incubate at 42° C. for 60 minutes and heat denature at 85° C. for 5 minutes, Dilute the cDNA 1/100 in nuclease free water.

Quantitative polymerase chain reaction (q-PCR), step 2 of the protocol, was performed as follows:

5 µL diluted cDNA was mixed with 5 µL SYBR Green Master Mix, UniRT (Exiqon AS, Cat. No. 203400) into the 384 well plate with desiccated primer sets of the seven miR assays described below. The plate was sealed and directly put on to the LightCycler for amplification and analysis.

q-RT-PCR reactions were performed in a LightCycler 480 (Roche Diagnostics) using the following PCR protocol:
1. 95° C. for 10 minutes
2. 95° C. for 10 seconds
3. 60° C. for 1 minute Signal detection with SYBR green (HRM dye) setup. Steps 2-3 repeated for 45 times followed by melting curve analysis.

Standard data analysis was performed on the LC480 raw data using the supplied data analysis software (Roche Diagnostics). Cp values were collected as Abs Quant/second derivatives max.

For this experiment of looking at examples of well expressed miRNA genes from both liver and heart, we used mean of raw data Cp values without normalization or calibration. This is done since normalization between tissues is not very accurate way of estimating miRs from different sources. Then we compare the difference between the two tissues in terms of Δ Cp values. Note that a difference of 1 in Cp value represents approximately a two fold difference in expression.

Results and Discussion

We selected total of 7 miRNAs that are known previously from the literature, to be differentially expressed between heart and liver tissue. The results are shown in table 15 and FIG. 7. The data obtained showed that the three genes miR-1, miR-133b and 126 are all showing much higher expression in heart samples than liver samples. Similarly the miR-192, miR-194 and miR-122 and 122* are showing much higher expression liver than heart. The difference is ranging from 2.6 to 12.9 Cp which corresponds to a range of from 5 fold to over 1000 fold difference in expression. In general the differentially expressed miRs described from the literature are easily distinguished by the UniRT expression platform using the assays described here.

TABLE 15

Expression values for the 7 miR selected and tested on the UniRT platform.

| miR name | Heart (Mean Cp) | Liver (Mean Cp) | Δ Cp |
|---|---|---|---|
| hsa-miR-1 | 20.9 | 33.9 | 12.9 |
| hsa-miR-133b | 22.0 | 34.7 | 12.7 |
| hsa-miR-126 | 22.5 | 25.1 | 2.6 |
| hsa-miR-192 | 31.6 | 25.3 | −6.3 |
| hsa-miR-122* | 37.6 | 30.0 | −7.5 |
| hsa-miR-194 | 32.3 | 25.9 | −6.4 |
| hsa-miR-122 | 31.8 | 21.1 | −10.8 |

Positive ΔCp values represent excess expression in heart and negative Cps represents excess expression in liver.

Example 10

Comparison of miR Specific Assays Designed in Present Invention to Competing Method Using Pure DNA Primers The LNA based design described in the present invention was compared to a commercial DNA based product, the miScript Reverse Transcription Kit (Qiagen, Cat. no. 218060, QIAGEN GmbH, Hilden, Germany). This DNA based product also relies on a miRNA 3'-polyadenylation step followed by reverse transcription with a DNA based poly dT primer where both reactions occur in a one-tube reaction. Because both these methods use the same enzymatic steps a comparison very well illustrate the surprising advantages of the present LNA based method since the miScript does not include LNA in the primers. Another difference is that the miScript uses a reverse primer specific to the universal tag added with the RT primer whereas the LNA based reverse primer of the present method is specific to the miRNA being detected.

TABLE 16

Nucleotide sequences of compared miRNAs

| miR | Sequence | SEQ ID NO | miR gc % | miR Tm |
|---|---|---|---|---|
| hsa-let-7a | 5'-ugagguaguagguuguauaguu-3' | 90 | 36 | 50 |
| hsa-miR-143 | 5'-ugagaugaagcacuguagcuc-3' | 122 | 39 | 54 |
| hsa-miR-155 | 5'-uuaaugcuaaucgugauaggggu-3' | 123 | 47 | 54 |
| hsa-mir-1 | 5'-uggaauguaaagaaguauguau-3' | 124 | 27 | 47 |

TABLE 17

Primer sets used in comparison

| miR | Forward primer (5'->3') | SEQ ID NO | Reverse primer (5'->3') | corresponding SEQ ID NO | Qiagen assay cat. no |
|---|---|---|---|---|---|
| hsa-let-7a | tGaGgtagtaggttg | 7 | cggaggtactagttttttttttttttAactat | 94 | MS 00006482 |
| hsa-miR-143 | tGaGatgaagcactg | 125 | tgacacggaggtactagttttttttttttttGagcta | 126 | MS 00003514 |
| hsa-miR-155 | gacttaaTgCtaatcgtgat | 127 | gtactagttttttttttttttAccccta | 128 | MS 00003605 |
| hsa-mir-1 | ctgtGgAatgtaaagaagt | 121 | tgacacggaggtactagttttttttttttttAtacata | 114 | MS000083 58 |

First Step

Reverse transcription was performed on a dilution series of synthetic miRNA target (obtained from Integrated DNA technologies Inc., Coralville, Iowa, US.), with a background of 10 ng/μl MS2 bacteriophage RNA (Roche Applied Science, Catalog Number 10165948001), using either Universal cDNA Synthesis Kit (Exiqon Vedbaek, Denmark., Prod. No. 203300) or miScript Reverse Transcription Kit (Qiagen, Cat. no. 218060, QIAGEN GmbH, Hilden, Germany) according to the manufacturer's instructions.

Second Step

On the cDNA obtained using the Universal cDNA Synthesis Kit (Exiqon, Prod. No. 203300), qPCR was performed using SYBR Green master mix, Universal RT (Exiqon, Prod. No. 203400) and the primer sets described in Table 17. On the cDNA obtained using miScript Reverse Transcription Kit (Qiagen, Cat. no. 218060), qPCR was performed using miScript SYBR Green PCR Kit (Qiagen, Cat. no. 218073). In both cases the amplification and detection was performed on a Roche LC480 LightCycler (Roche Diagnostics A/S, Hvidovre, Denmark), using the cycling conditions instructed by the manufacturer. Each cDNA/assay combination was run in triplicate.

Results

FIG. 8 shows the triplicate Cp values versus template concentration obtained in the experiment for each of the four tested miRNAs. In all four compared assays, the method of the present invention was more sensitive (black lines connecting diamonds) than the miScript assay (gray lines connecting spheres) as indicated by the lower Cp values consistently obtained with the assay of the present invention. In the case of hsa-let-7a, there was a 10-fold improved sensitivity of the assay of the present invention, measured as the lowest copy-number detected quantitatively. For hsa-miR-143 and hsa-miR-155 the difference in sensitivity was 100-fold better with the assay of the present invention. For hsa-miR-1 with a very low gc-content (see table 16) and thus low melting temperature, the alternative assay was unable to detect the template even at highest concentration of RNA. The assay designed in the present invention quantitatively detected an equivalent of as little as 10 miRNA copies in the PCR reaction. This data clearly shows that the assay of the present invention is surprisingly more sensitive. We ascribe the improvement in sensitivity partly to the design of the extension primer which comprise both a 5'"tag-sequence" ($R^1$) as well as a 3'"anchor sequence" ($R^2$) and partly to the design of template-specific (e.g. miR-specific) forward and reverse primers of the qPCR reaction which includes LNA. Our results indicate that the gene specific design of the forward and reverse primers allow more sensitive detection than with pure DNA primers using a universal reverse primer.

Table 18: Nucleotide Sequences

Lower case designates natural occurring nucleotides, upper case designates LNA, mC denotes LNA methyl cytosine. v is either an adenine residue, a guanine residue, or a cytosine residue and n is either an adenine residue, a guanine residue, a cytosine residue or a thymine residue.

| Primer/Sequence name | Nucleotide sequence (5' → 3') | SEQ ID NO |
|---|---|---|
| hsa-miR-197; forward primer | ttmCaccaccttctcca | 1 |
| hsa-miR-197 reverse primer | cttttttttttttttttGctgggt | 2 |
| Reverse primer R[3] sequence | Tgacacggaggtactag | 3 |
| Reverse primer tail | Tgacacggaggtactagttttttttttttttt | 4 |
| L2TA extension primer | Ggtactagttttttttttttttvn | 5 |
| hsa-let-7a DNA template | tgcggtgacaccgaggtactagttttttttttttttttaactatacaacctactacctca | 6 |
| hsa-let-7a forward primer | tGaGgtagtaggttg | 7 |
| hsa let 7a reverse primer | Cggtgacacggaggtactagttttttttttttttttaactata | 8 |
| hsa-let-7a reverse primer | cggtgacacggaggtactagttttttttttttttttaamCtata | 9 |
| hsa-miR-16 forward primer | tAgmCagcacgtaaa | 10 |
| hsa-miR-16 reverse primer | cacggaggtactagttttttttttttttttcgccaat | 11 |
| hsa-miR-16 reverse primer | cacggaggtactagttttttttttttttttmCgccaat | 12 |
| hsa-miR-21 forward primer | tAgmCttatcagactgatg | 13 |
| hsa-miR-21 reverse primer | gcggtgacacggaggtactagttttttttttttttttcaac | 14 |
| hsa-miR-21 reverse primer | gcggtgacacggaggtactagttttttttttttttttmCaac | 15 |
| hsa-miR-23a forward primer | atmCamCattgccag | 16 |
| hsa-miR-23a reverse primer | tgacacggaggtactagttttttttttttttttggaaatc | 17 |
| hsa-miR-23a reverse primer | tgacacggaggtactagttttttttttttttttGgaaatc | 18 |
| hsa-miR-150 forward primer | tmCtmCccaacccttg | 19 |
| hsa-miR-150 reverse primer | tgacacggaggtactagttttttttttttttttmCactggta | 20 |
| hsa-miR-150 reverse primer | tgacacggaggtactagttttttttttttttttcactggta | 21 |
| hsa-miR-208a forward primer | ataaGamCgAgcaaaaag | 22 |
| hsa-miR-208a reverse primer | mCggtgacacggaggtactagttttttttttttttttacaagc | 23 |
| hsa-miR-208a reverse primer | cggtgacacggaggtactagttttttttttttttttAcaagc | 24 |
| hsa-miR-208a reverse primer | cggtgacacggaggtactagttttttttttttttttacaagc | 25 |
| hsa-miR-124 forward primer | taaGgcacgcggtga | 26 |

-continued

| Primer/Sequence name | Nucleotide sequence (5' → 3') | SEQ ID NO |
|---|---|---|
| hsa-miR-9 forward primer | ctgtmCtttGgttatctag | 27 |
| hsa-miR-181a forward primer | aamCattmCaacgctgt | 28 |
| hsa-miR-128 forward primer | tmCamCagtgaaccggt | 29 |
| hsa-miR-488 forward primer | ttGaaaGgctatttc | 30 |
| hsa-miR-328 forward primer | ctggccctctctgcc | 31 |
| hsa-miR-324 forward primer | cgcatcccctagggcat | 32 |
| hsa-miR-331 forward primer | cTaGgtatggtccca | 33 |
| hsa-miR-34a forward primer | tGgcAgtgtcttagc | 34 |
| hsa-miR-130a forward primer | caGtGcaatgttaaaag | 35 |
| hsa-miR-1 forward primer | tGgAatgtaaagaagt | 36 |
| hsa-miR-23b forward primer | atmCamCattgccag | 37 |
| hsa-miR-133a forward primer | tTtGgtccccttcaa | 38 |
| hsa-miR-133b forward primer | tTtGgtccccttcaa | 39 |
| hsa-miR-93 forward primer | cAaaGtgctgttcgtg | 40 |
| hsa-miR-181b forward primer | aamCattmCattgctgtc | 41 |
| hsa-miR-24 forward primer | tGgctmCagttcagca | 42 |
| hsa-miR-124 reverse primer | tgacacggaggtactagttttttttttttttTggcat | 43 |
| hsa-miR-9 reverse primer | tgacacggaggtactagttttttttttttttmCatacag | 44 |
| hsa-miR-181a reverse primer | tgacacggaggtactagtttttttttttttttamCtcac | 45 |
| hsa-miR-128 reverse primer | tgacacggaggtactagtttttttttttttttAaagaga | 46 |
| hsa-miR-488 reverse primer | tgacacggaggtactagttttttttttttttttGacca | 47 |
| hsa-miR-328 reverse primer | tgacacggaggtactagttttttttttttttttAcggaa | 48 |
| hsa-miR-324 reverse primer | tgacacggaggtactagttttttttttttttttAcacca | 49 |
| hsa-miR-331 reverse primer | tgacacggaggtactagttttttttttttttttGgatc | 50 |
| hsa-miR-34a reverse primer | tgacacggaggtactagtttttttttttttttamCaacca | 51 |

| Primer/Sequence name | Nucleotide sequence (5' → 3') | SEQ ID NO |
|---|---|---|
| hsa-miR-130a reverse primer | tgacacggaggtactagttttttttttttttttAtgc | 52 |
| hsa-miR-1 reverse primer | tgacacggaggtactagttttttttttttttttAtacata | 53 |
| hsa-miR-23b reverse primer | tgacacggaggtactagtttttttttttttttggTaatc | 54 |
| hsa-miR-133a reverse primer | tgacacggaggtactagttttttttttttttttGagctg | 55 |
| hsa-miR-133b reverse primer | tgacacggaggtactagttttttttttttttttAgctg | 56 |
| hsa-miR-93 reverse primer | tgacacggaggtactagttttttttttttttttmCtacctg | 57 |
| hsa-miR-181b reverse primer | tgacacggaggtactagttttttttttttttttAccca | 58 |
| hsa-miR-24 reverse primer | tgacacggaggtactagttttttttttttttttmCtgttc | 59 |
| hsa-miR-146b forward primer | ctgtGagaactgaattcca | 60 |
| hsa-miR-146b-3p forward primer | tgccctgtggactca | 61 |
| hsa-miR-429 forward primer | ctgtaatamCtGtctggta | 62 |
| hsa-miR-193a-3p forward primer | aactggcctacaaagtcc | 63 |
| hsa-miR-193a forward primer | gtctttgcgggcga | 64 |
| hsa-miR-193b forward primer | aamCtggccctcaaag | 65 |
| hsa-miR-149 forward primer | tmCtggcTccgtgtcttca | 66 |
| hsa-miR-452 forward primer | aamCtGtttgcagaggaa | 67 |
| hsa-miR-452* forward primer | ctmCatmCtGcaaagaagta | 68 |
| hsa-miR-30b forward primer | tGtaaamCatcctacactc | 69 |
| hsa-miR-34b forward primer | ctgcaatcactaactccact | 70 |
| hsa-miR-34c forward primer | aggcaGtgtagttagctg | 71 |
| hsa-miR-134 forward primer | tgtgactggttgaccaga | 72 |
| hsa-miR-671 forward primer | ctgaGgaagccctgga | 73 |
| hsa-miR-769-3p forward primer | ctgggatctccggggtct | 74 |
| hsa-miR-146b reverse primer | cgtactagttttttttttttttttAgcct | 75 |
| hsa-miR-146b-3p reverse primer | gtactagttttttttttttttttmCcagaac | 76 |

| Primer/Sequence name | Nucleotide sequence (5' → 3) | SEQ ID NO |
|---|---|---|
| hsa-miR-429 reverse primer | gtactagtttttttttttttttAcggtt | 77 |
| hsa-miR-193a-3p reverse primer | gtactagtttttttttttttttamCtgg | 78 |
| hsa-miR-193a reverse primer | ggtactagtttttttttttttttmCatct | 79 |
| hsa-miR-193b reverse primer | gaggtactagtttttttttttttttmCatct | 80 |
| hsa-miR-149 reverse primer | tagttttttttttttttgggAgtg | 81 |
| hsa-miR-452 reverse primer | gtactagttttttttttttttttmCagtt | 82 |
| hsa-miR-452* reverse primer | gtactagttttttttttttttttmCactt | 83 |
| hsa-miR-30b reverse primer | gtactagtttttttttttttttaGctga | 84 |
| hsa-miR-34b reverse primer | gaggtactagttttttttttttttttAtgg | 85 |
| hsa-miR-34c reverse primer | tactagtttttttttttttttGcaatca | 86 |
| hsa-miR-134 reverse primer | gtactagtttttttttttttttTcccct | 87 |
| hsa-miR-671 reverse primer | gtactagttttttttttttttttmCtcca | 88 |
| hsa-miR-769-3p reverse primer | aggtactagttttttttttttttttAacca | 89 |
| hsa-let-7a | ugagguaguagguuguauaguu | 90 |
| hsa-let-7f | ugagguaguagauuguauaguu | 91 |
| hsa-let-7c | ugagguaguagguuguaugguu | 92 |
| hsa-let-7e | ugagguaggagguuguauaguu | 93 |
| hsa-let-7a reverse primer | cggaggtactagttttttttttttttttAactat | 94 |
| hsa-miR-27b forward primer | ttmCamCagtggctaag | 95 |
| hsa-miR-27b reverse primer | tgacacggaggtactagttttttttttttttttGcaga | 96 |
| hsa-miR-195 forward primer | ctgtaGcaGcacagaa | 97 |
| hsa-miR-195 reverse primer | tgacacggaggtactagttttttttttttttttGccaat | 98 |
| hsa-miR-10a forward primer | tAccctGtagatccgaa | 99 |
| hsa-miR-10a reverse primer | tgacacggaggtactagtttttttttttttttttmCacaaat | 100 |
| hsa-pre-miR-10a forward primer | tgtGtaaggaattttgtggt | 101 |
| hsa-pre-miR-10a reverse primer | gaggtactagtttttttttttttttttAttc | 102 |

-continued

| Primer/Sequence name | Nucleotide sequence (5' → 3) | SEQ ID NO |
|---|---|---|
| Has-miR-203 RNA | gugaaauguuuaggaccacuag | 103 |
| Pre-mIR-203 RNA | agugguucuuaacaguucaacaguucugu-agcgcaauugugaaauguuuaggaccacuag | 104 |
| hsa-miR-203 reverse primer | tgacacggaggtactagtttttttttttttttCtag | 105 |
| hsa-miR-203 forward primer | gtGaaatGtttaggacca | 106 |
| hsa-pre-miR-203 forward primer | cagttcaacagttctgtagc | 107 |
| hsa-miR-122 reverse primer | tgacacggaggtactagtttttttttttttttCaaacac | 108 |
| hsa-miR-194 reverse primer | gtactagtttttttttttttttCcaca | 109 |
| hsa-miR-122* reverse primer | gaggtactagtttttttttttttttAtttag | 110 |
| hsa-miR-192 reverse primer | gtactagtttttttttttttttGgct | 111 |
| hsa-miR-126 reverse primer | gtactagtttttttttttttttTcgcat | 112 |
| hsa-miR-133b reverse primer | tgacacggaggtactagtttttttttttttttAgctg | 113 |
| hsa-miR-1 reverse primer | tgacacggaggtactagtttttttttttttttAtacata | 114 |
| hsa-miR-122 forward primer | tGgaGtgtgacaatg | 115 |
| hsa-miR-194 forward primer | tGtaaCagcaactcca | 116 |
| hsa-miR-122* forward primer | aAcgccAtTatcacact | 117 |
| hsa-miR-192 forward primer | tgactGacCtatgaattgac | 118 |
| hsa-miR-126 forward primer | ctgtCgtaccgtgagta | 119 |
| hsa-miR-133b forward primer | tTtGgtccccttcaa | 120 |
| hsa-miR-1 forward primer | ctgtGgAatgtaaagaagt | 121 |
| hsa-miR-143 | 5'-ugagaugaagcacuguagcuc-3' | 122 |
| hsa-miR-155 | 5'-uuaaugcuaaucgugauaggggu-3' | 123 |
| hsa-mir-1 | 5'-uggaauguaaagaaguauguau-3' | 124 |
| hsa-miR-143 forward primer | tGaGatgaagcactg | 125 |
| hsa-miR-143 reverse primer | tgacacggaggtactagtttttttttttttttGagcta | 126 |
| hsa-miR-155 forward primer | gacttaaTgCtaatcgtgat | 127 |
| hsa-miR-155 reverse primer | gtactagtttttttttttttttAccccta | 128 |

| Primer/Sequence name | Nucleotide sequence (5' → 3') | SEQ ID NO |
|---|---|---|
| L6TA extension primer | tgcggtgacacggaggtactagtttttttttttttttVN | 129 |

The invention claimed is:

1. A method for amplification of a specific microRNA molecule in a sample, the method comprising the steps of:
   a) adding poly-A tails to a population of microRNA molecules in a sample;
   b) producing cDNA molecules of the poly-A-tailed microRNA molecules using an extension primer in a reverse transcription reaction; and
   c) amplifying the cDNA molecules by PCR using a forward primer and a reverse primer both of which are microRNA-specific primers for said specific microRNA molecule, wherein said extension primer is a nucleotide sequence according to formula III:

$$R^1\text{-}(T)_y\text{-}R^2 \quad (III)$$

wherein $R^1$ is a 5'-end nucleotide sequence, $(T)_y$ is a central part of y consecutive thymine residues, wherein y is an integer of from 1 to 100, and wherein $R^2$ is a sequence motif VN or VNN, consisting of two or three 3'-end terminal nucleotide residues respectively, wherein V is either an adenine residue, a guanine residue, or a cytosine residue and N is either an adenine residue, a guanine residue, a cytosine residue or a thymine residue;

wherein the reverse primer is a nucleotide sequence according to formula II:

$$R^3\text{-}(T)_x\text{-}R^4 \quad (II)$$

wherein $R^3$ is a 5'-end nucleotide sequence, $(T)_x$ is a central part of x consecutive thymine residues, wherein x is an integer of from 1 to 100, and $R^4$ is a 3'-end nucleotide sequence that specifically hybridizes to a nucleotide sequence of a target microRNA molecule; and wherein either the forward primer and/or $R^4$ of the reverse primer comprise at least one LNA.

2. The method of claim 1, wherein both the forward primer and $R^4$ of the reverse primer each comprise at least one LNA.

3. The method according to claim 2, wherein the extension primer comprises at least one LNA.

4. The method according to claim 1, wherein the extension primer comprises at least one LNA.

5. The method according to claim 1, wherein the forward primer comprises at least one LNA.

6. The method according to claim 1, wherein $R^4$ comprises at least one LNA.

7. The method according to claim 4, wherein the forward primer has a length in the range of from 10 to 100 nucleotides.

8. The method according to claim 1, wherein the extension primer has a length in the range from 10 to 100 nucleotides.

9. The method according claim 8, wherein the extension primer has a length in the range from 15 to 45 nucleotides.

10. The method according to claim 9, wherein $R^1$ is a nucleotide sequence with a length of from 1 to 30 nucleotides.

11. The method according to claim 10, wherein $R^1$ is a nucleotide sequence with a length of from 6 to 10 nucleotides.

12. The method according to claim 11, wherein $R^1$ is a nucleotide sequence with a length of 8 nucleotides.

13. The method according to claim 12, wherein y is an integer from 5 to 50.

14. The method according to claim 13, wherein y is an integer from 5 to 21.

15. The method according to claim 14, wherein y is 12, 13, 14, 15, 16, 17 or 18.

16. The method according to claim 15, wherein y is 15.

17. The method according to claim 16, wherein $R^2$ is a sequence motif VN, consisting of two 3'-end terminal nucleotide residues, wherein V is either an adenine residue, a guanine residue, or a cytosine residue and N is either an adenine residue, a guanine residue, a cytosine residue or a thymine residue.

18. The method according to claim 16, wherein $R^2$ is a sequence motif VNN, consisting of the three 3'-end terminal nucleotides, wherein V is either an adenine residue, a guanine residue, or a cytosine residue and N is either an adenine residue, a guanine residue, a cytosine residue or a thymine residue.

19. The method according to claim 18, wherein the forward primer is designed to specifically hybridize to the cDNA molecule of a target microRNA molecule.

20. The method according to claim 17, wherein the forward primer is designed to specifically hybridize to the cDNA molecule of a target microRNA molecule.

21. The method according to claim 20, wherein $R^3$ is a nucleotide sequence with a length of from 1 to 30 nucleotides.

22. The method according to claim 21, wherein x is 5 to 50.

23. The method according to claim 22, wherein x is 5 to 21.

24. The method according to claim 23, wherein x is 15.

25. The method according to claim 24 wherein x of formula (II) equals y of formula (III).

26. The method according to claim 25, wherein $R^4$ has a length in the range of from 1 to 10 nucleotides.

27. The method according to claim 26, wherein $R^4$ comprises at least one LNA.

28. The method according to claim 27, wherein $R^4$ contains only one LNA.

29. The method according to claim 28, wherein $R^4$ is designed to specifically hybridize to the 3'-end of a target microRNA.

30. The method according to claim 29, wherein the LNA is situated in the 5' position or the position adjacent to the 5' position of the $R^4$ part of the reverse primer.

31. A method for measuring the amount of a target microRNA in a sample from a living organism, the method comprising the steps of:
   1) amplifying the target microRNA according to the method of claims 30, and
   2) measuring the amount of the amplified DNA molecules.

32. The method according to claim 31, wherein the amount of the amplified DNA molecules is measured using a fluorescence-based quantitative real-time PCR method.

33. The method according to claim 32, wherein the amount of the amplified DNA molecules is measured using SYBR® green dye.

34. A method for measuring the amount of a target microRNA in a sample from a living organism, the method comprising the steps of:
   1) amplifying the target microRNA according to the method of claim 1
   2) measuring the amount of the amplified DNA molecules.

35. The method according to claim 34, wherein the amount of the amplified DNA molecules is measured using a fluorescence-based quantitative real-time PCR method.

36. The method according to claim 35, wherein the amount of the amplified DNA molecules is measured using SYBR® green dye.

* * * * *